United States Patent
Watterson et al.

(10) Patent No.: US 7,166,064 B2
(45) Date of Patent: Jan. 23, 2007

(54) SYSTEMS AND METHODS FOR ENABLING TWO-WAY COMMUNICATION BETWEEN ONE OR MORE EXERCISE DEVICES AND COMPUTER DEVICES AND FOR ENABLING USERS OF THE ONE OR MORE EXERCISE DEVICES TO COMPETITIVELY EXERCISE

(75) Inventors: Scott R. Watterson, Logan, UT (US); William T. Dalebout, Logan, UT (US); Darren C. Ashby, Richmond, UT (US); Robert D. Ashby, Collinston, UT (US)

(73) Assignee: Icon IP, Inc., Logan, UT (US)

( * ) Notice: Subject to any disclaimer, the term of this patent is extended or adjusted under 35 U.S.C. 154(b) by 411 days.

(21) Appl. No.: 09/947,193

(22) Filed: Sep. 5, 2001

(65) Prior Publication Data

US 2002/0045519 A1 Apr. 18, 2002

Related U.S. Application Data

(63) Continuation-in-part of application No. 09/641,600, filed on Aug. 18, 2000, which is a continuation-in-part of application No. 09/641,220, filed on Aug. 18, 2000, which is a continuation-in-part of application No. 09/641,627, filed on Aug. 18, 2000, which is a continuation-in-part of application No. 09/496,560, filed on Feb. 2, 2000, which is a continuation-in-part of application No. 09/349,608, filed on Jul. 8, 1999, now Pat. No. 6,312,363.

(51) Int. Cl.
*A63B 22/00* (2006.01)

(52) U.S. Cl. .......................................... 482/54; 482/51
(58) Field of Classification Search ................ 482/1–9, 482/51, 54, 900–902
See application file for complete search history.

(56) References Cited

U.S. PATENT DOCUMENTS

| 3,518,985 A | 7/1970 | Quinton |
| 3,602,502 A | 8/1971 | Hampl |

(Continued)

OTHER PUBLICATIONS

*The FitLinxx Interactive Fitness Network* TM, *Integrated Fitness Corp.*, brochure, 1998.
Fitlinxx Interactive Fitness Network TM, *The Difference Between Surviving and Thriving May be as Simple as FitLinxx* TM, *Integrated Fitness Corp.*, brochure, 1998.

(Continued)

*Primary Examiner*—Glenn E. Richman
(74) *Attorney, Agent, or Firm*—Workman Nydegger

(57) ABSTRACT

Systems and methods for providing two-way communication between an exercise device and a computer device. A computer device and an exercise device employ different protocol formats and communicate through a translator device, which includes a microcontroller specifically designed to translate data or signals deliverable by different communication protocols. The exercise device, the computer device, or a user at either the exercise or computer device may initiate the communication. The enabled communication allows for such features as the performance of an automatic diagnostic analysis on the exercise device, the programming of internal parameters of the exercise device upon identifying specific components, the monitoring of any measurable parameter of the user, the providing of instructional direction and/or encouragement relating to a particular exercise routine, the controlling of the amount of resistance experienced by the user of the exercise device, and other interactions facilitated by the translator device.

20 Claims, 12 Drawing Sheets

U.S. PATENT DOCUMENTS

| | | | |
|---|---|---|---|
| 3,802,698 A | 4/1974 | Burian et al. | 272/57 R |
| 3,845,756 A | 11/1974 | Olsson | 600/520 |
| 4,112,928 A | 9/1978 | Putsch | |
| 4,151,988 A | 5/1979 | Nabinger | |
| 4,358,105 A | 11/1982 | Sweeney, Jr. | |
| 4,408,613 A | 10/1983 | Relyea | 600/483 |
| 4,544,152 A | 10/1985 | Taitel | |
| 4,549,044 A | 10/1985 | Durham | |
| 4,556,216 A | 12/1985 | Pitkanen | 482/131 |
| 4,571,682 A | 2/1986 | Silverman et al. | |
| 4,642,769 A | 2/1987 | Petrofsky | |
| 4,659,074 A | 4/1987 | Taitel et al. | |
| 4,687,195 A | 8/1987 | Potts | |
| 4,708,337 A | 11/1987 | Shyu | |
| 4,709,917 A | 12/1987 | Yang | 482/63 |
| 4,757,495 A | 7/1988 | Decker et al. | 370/477 |
| 4,763,284 A | 8/1988 | Carlin | 702/41 |
| 4,828,257 A * | 5/1989 | Dyer et al. | 482/5 |
| 4,837,157 A | 6/1989 | Turnell et al. | 436/20 |
| 4,842,266 A | 6/1989 | Sweeney, Sr. et al. | |
| 4,842,274 A | 6/1989 | Oosthuizen et al. | |
| 4,848,737 A | 7/1989 | Ehrenfield | |
| 4,860,763 A | 8/1989 | Schminke | |
| 4,866,704 A | 9/1989 | Bergman | 370/452 |
| 4,919,418 A | 4/1990 | Miller | 482/6 |
| 4,925,183 A | 5/1990 | Kim | 482/61 |
| 4,927,136 A | 5/1990 | Leask | |
| 4,934,694 A | 6/1990 | McIntosh | |
| 4,959,713 A | 9/1990 | Morotomi et al. | |
| 4,998,725 A | 3/1991 | Watterson et al. | |
| 5,020,795 A | 6/1991 | Airy et al. | |
| 5,054,774 A | 10/1991 | Belsito | |
| 5,062,632 A | 11/1991 | Dalebout et al. | |
| 5,067,710 A | 11/1991 | Watterson et al. | |
| 5,078,152 A | 1/1992 | Bond et al. | |
| 5,086,385 A | 2/1992 | Launey et al. | |
| 5,089,960 A | 2/1992 | Sweeney, Jr. | 463/6 |
| 5,104,120 A | 4/1992 | Watterson et al. | |
| 5,113,427 A | 5/1992 | Ryoichi et al. | |
| 5,145,475 A | 9/1992 | Cares | |
| 5,149,084 A | 9/1992 | Dalebout et al. | |
| 5,180,347 A | 1/1993 | Chen | 482/5 |
| 5,195,935 A | 3/1993 | Fencel | |
| 5,213,555 A | 5/1993 | Hood et al. | |
| 5,240,417 A | 8/1993 | Smithson et al. | 434/61 |
| 5,308,296 A | 5/1994 | Eckstein | |
| 5,313,942 A | 5/1994 | Platzker | |
| 5,314,391 A | 5/1994 | Potash et al. | |
| D348,493 S | 7/1994 | Ashby | |
| 5,328,420 A | 7/1994 | Allen | |
| 5,328,422 A | 7/1994 | Nichols | |
| 5,352,166 A | 10/1994 | Chang | |
| 5,361,091 A | 11/1994 | Hoarty et al. | 725/119 |
| 5,375,068 A | 12/1994 | Palmer et al. | 709/204 |
| 5,382,209 A | 1/1995 | Pasier et al. | |
| 5,387,164 A | 2/1995 | Brown, Jr. | 482/9 |
| 5,410,471 A | 4/1995 | Alyfuku et al. | |
| 5,410,472 A | 4/1995 | Anderson | |
| 5,433,679 A | 7/1995 | Szymczak et al. | |
| 5,462,051 A | 10/1995 | Oka et al. | |
| 5,462,503 A | 10/1995 | Benjamin et al. | 482/4 |
| 5,462,504 A | 10/1995 | Trulaske et al. | |
| 5,466,200 A * | 11/1995 | Ulrich et al. | 482/4 |
| 5,474,090 A | 12/1995 | Begun et al. | |
| 5,489,249 A | 2/1996 | Brewer et al. | |
| 5,512,025 A | 4/1996 | Dalebout et al. | |
| 5,527,239 A | 6/1996 | Abbondanza | |
| 5,535,664 A | 7/1996 | Rokowski | |
| 5,546,324 A | 8/1996 | Palmer et al. | 348/14.1 |
| 5,572,643 A | 11/1996 | Judson | 709/218 |
| 5,590,128 A | 12/1996 | Maloney et al. | 370/260 |
| 5,591,104 A | 1/1997 | Andrus et al. | |
| 5,598,849 A | 2/1997 | Browne | 600/520 |
| 5,600,310 A | 2/1997 | Whipple, III et al. | |
| 5,605,336 A | 2/1997 | Gaoiran et al. | 273/445 |
| 5,619,412 A | 4/1997 | Hapka | |
| 5,619,991 A | 4/1997 | Sloane | |
| 5,626,539 A | 5/1997 | Piaget et al. | |
| 5,645,509 A | 7/1997 | Brewer et al. | |
| 5,655,997 A | 8/1997 | Greenberg et al. | 482/5 |
| 5,663,951 A | 9/1997 | Danneels et al. | 370/230 |
| 5,690,582 A | 11/1997 | Ulrich et al. | 482/4 |
| 5,695,400 A | 12/1997 | Fennell, Jr. et al. | 463/42 |
| 5,697,834 A | 12/1997 | Heumann et al. | |
| 5,702,323 A | 12/1997 | Poulton | |
| 5,720,771 A | 2/1998 | Snell | |
| 5,722,418 A | 3/1998 | Bro | |
| 5,738,612 A | 4/1998 | Tsuda | |
| 5,743,833 A | 4/1998 | Watterson et al. | |
| 5,749,372 A | 5/1998 | Allen et al. | 482/8 |
| 5,752,897 A | 5/1998 | Skowronski et al. | |
| 5,754,765 A | 5/1998 | Danneels et al. | 709/222 |
| 5,759,199 A | 6/1998 | Snell et al. | |
| 5,771,354 A | 6/1998 | Crawford | 709/229 |
| 5,779,596 A | 7/1998 | Weber | |
| 5,810,696 A | 9/1998 | Webb | |
| 5,836,770 A | 11/1998 | Powers | |
| 5,838,906 A | 11/1998 | Doyle et al. | 715/501.1 |
| 5,845,230 A | 12/1998 | Lamberson | |
| 5,854,833 A | 12/1998 | Hogan et al. | 379/114.14 |
| 5,857,939 A | 1/1999 | Kaufman | 482/8 |
| 5,865,733 A | 2/1999 | Malinouskas et al. | |
| 5,873,369 A | 2/1999 | Laniado et al. | |
| 5,880,677 A | 3/1999 | Lestician | |
| 5,888,172 A | 3/1999 | Andrus et al. | |
| 5,890,995 A | 4/1999 | Bobick et al. | |
| 5,905,442 A | 5/1999 | Mosebrook et al. | |
| 5,909,544 A | 6/1999 | Anderson, II et al. | 709/208 |
| 5,911,132 A | 6/1999 | Sloane | |
| 5,911,687 A | 6/1999 | Sato et al. | |
| 5,916,063 A | 6/1999 | Alessandri | 482/4 |
| 5,917,405 A | 6/1999 | Joao | |
| 5,929,748 A | 7/1999 | Odinak | |
| 5,929,782 A | 7/1999 | Stark | |
| 5,931,763 A * | 8/1999 | Alessandri | 482/4 |
| 5,956,509 A | 9/1999 | Kevner | 719/330 |
| 5,961,561 A | 10/1999 | Wakefield, II | |
| 5,964,701 A | 10/1999 | Asada et al. | |
| 5,967,975 A | 10/1999 | Ridgeway | |
| 5,995,868 A | 11/1999 | Dorfmeister et al. | |
| 5,997,476 A | 12/1999 | Brown | |
| 6,010,451 A | 1/2000 | Clawson | |
| 6,013,007 A | 1/2000 | Root et al. | |
| 6,014,432 A | 1/2000 | Modney | |
| 6,033,344 A | 3/2000 | Trulaske et al. | |
| 6,042,519 A | 3/2000 | Shea | 482/57 |
| 6,050,822 A | 4/2000 | Faughn | |
| 6,050,924 A | 4/2000 | Shea | |
| 6,053,737 A | 4/2000 | Babbitt et al. | |
| 6,053,844 A | 4/2000 | Clem | |
| 6,059,692 A | 5/2000 | Hickman | |
| 6,066,075 A | 5/2000 | Poulton | 482/8 |
| 6,106,297 A | 8/2000 | Pollak et al. | |
| 6,132,337 A | 10/2000 | Krupka et al. | 482/8 |
| 6,152,856 A | 11/2000 | Studor et al. | |
| 6,171,218 B1 | 1/2001 | Shea | 482/57 |
| 6,193,631 B1 | 2/2001 | Hickman | |
| 6,211,451 B1 | 4/2001 | Tohgi et al. | |
| 6,231,481 B1 | 5/2001 | Brock | 482/8 |
| 6,231,482 B1 | 5/2001 | Thompson | |
| 6,251,048 B1 | 6/2001 | Kaufman | 482/8 |

| | | |
|---|---|---|
| 6,312,363 B1 | 11/2001 | Watterson et al. ............ 482/54 |
| 6,358,187 B1 | 3/2002 | Smith ............................ 482/4 |
| 6,458,060 B1 | 10/2002 | Watterson et al. ............ 482/54 |
| 6,464,618 B1 | 10/2002 | Shea |
| 6,475,115 B1 | 11/2002 | Candito et al. ................ 482/4 |
| 6,497,638 B1 | 12/2002 | Shea |
| 6,582,342 B1 | 6/2003 | Kaufman et al. ............. 482/8 |
| 6,601,016 B1 | 7/2003 | Brown et al. |
| 6,616,578 B1 | 9/2003 | Alessandri ..................... 482/8 |
| 6,634,992 B1 | 10/2003 | Ogawa ........................... 482/8 |
| 6,638,198 B1 | 10/2003 | Shea .............................. 482/8 |
| 6,645,124 B1 | 11/2003 | Clem ............................. 482/4 |

OTHER PUBLICATIONS

Forbes Digital Tool: Startups, *Sweat.equity*, www.forbes.com, Feb. 1998.

Netpulse, *Networkingout—Coming Distractions: Netpulse Helps Exercisers Surf the Net at the Gym, Accomplish Several Goals at Once*, www.netpulse.com, Apr. 1998.

Netpulse, *Instead of having an equipment repair technician traveling over hill and date, you may soon have equipment repaired via the internet*, www.netpulse.com, Jul. 1998.

Netpulse, *Infotech is supposed to make life easier–remember? Here's how to be sure it does.*, www.netpulse, Aug. 1998.

Netpulse, Exercise station connects to the Net, *Now you can sweat to the Net.*, www.netpulse.com, Sep. 1998.

Netpulse, New Fitness Equipment Combines Internet, Sweat, *Now you can surf and sweat*, www.netpulse.com, Jan. 1999.

Netpulse, Hop In, Log On and Sweat, *Netpulse exercise machines are the latest Web feat*, www.netpulse.com, Feb. 1999.

Netpulse ClubWatch TM, *Internet Powered Service*, brochure, Apr. 1999.

Netpulse, *State of the Art*, www.netpulse.com, Feb. 2000.

Netpulse, *Netpulse Files for Patents on its Pioneering Technology Inventions and Groundbreaking Business Methods in the Media and Fitness Markets*, www.netpulse.com, May 2000.

Little Tony, One on One Video Trainer (for Model No. T1T12340), Jun. 1995 (25 pages).

*Men's Journal,* Squat.com. The Home Gym Goes Online, May 2000 (2 pages).

MSNBC.com, Smart Fitness Section, On A Quest for Fitness – The latest workout gear and Gadgets, Feb. 29, 2000 (6 pages).

OPTIONS Manual: Video Track/Track Five/Personal Trainer Plus (Part No. 109917) cited as "OPTIONS"), Sep. 1992 (2 pages).

*PR Newswire,* Turn Your Treadmill Into a Internet Appliance with www.iFIT.com, Oct. 19, 1999 (3 pages).

PRO–FORM 8.0 TXP Manual (for Model No. PF080010) (cited as "8.0TXP"), Nov. 1991 (16 pages).

*The Boston Globe,* Living Section, p. F1, Wired Workout Local Gyms, Mar. 11, 2000 (2 pages).

*The Herald Journal,* People in Business, ICON winds Awards, vol. 91, No. 128, May 7, 2000 (1 page).

*US Weekly,* p. 71, Work Out Online, Mar. 27, 2000 (2 pages).

*Communications of the ACM,* vol. 35, No. 6, cited as "Comm of the ACM", Jun. 1992 (10 pages).

*Ebsco Publishing,* New home exercise equipment: your computer?, Jun. 2000 (3 pages).

*Fortune Magazine,* p. 84, Virtual Workouts –Treadmills Possesed, Apr. 17, 2000 (2 pages).

*Good House Keeping,* p. 53, A Run for the Money, Feb. 2000 (2 pages).

*IEEE Publication,* A Teleobotics Construction Set with Integrated Performance Analysis, 0–8186–7108–4/95 (IEEE) (cited as "Telerobotic Con."), Apr. 1995 (7 pages).

*IEEE Publication,* Intelligent Monitoring System for Limited System for Limited Communication Path: Telerobotic Task Execution over Internet, 0–8186–7108–4/95 (IEEE) (cited as "Intelligent"), Apr. 1995 (6 pages).

Lifestyler 10.0 ESP Manual (for Model No. 297052) (cited as "10.0 ESP"), Nov. 1992 (16 pages).

1994 Pro–Form First in Fitness, (1994 Copyright ProForm Products, Inc.), (16 pages).

\* cited by examiner

US 7,166,064 B2

SYSTEMS AND METHODS FOR ENABLING TWO-WAY COMMUNICATION BETWEEN ONE OR MORE EXERCISE DEVICES AND COMPUTER DEVICES AND FOR ENABLING USERS OF THE ONE OR MORE EXERCISE DEVICES TO COMPETITIVELY EXERCISE

CROSS-REFERENCE TO RELATED APPLICATIONS

This application is a continuation-in-part application of U.S. patent application Ser. No. 09/641,600, filed Aug. 18, 2000, entitled "Computer Systems and Methods for Interaction with Exercise Device," a continuation-in-part application of U.S. patent application Ser. No. 09/641,220, filed Aug. 18, 2000, entitled "Systems and Methods for Interaction with Exercise Device," and a continuation-in-part application of U.S. patent application Ser. No. 09/641,627, filed Aug. 18, 2000, entitled "System for Interaction with Exercise Device," each of which is a continuation-in-part application of U.S. patent application Ser. No. 09/349,608, filed Jul. 8, 1999 now U.S. Pat. No. 6,312,363, entitled "Systems and Methods for Providing an Improved Exercise Device with Motivational Programming" and a continuation-in-part application of U.S. patent application Ser. No. 09/496,560, filed Feb. 2, 2000, entitled "System and Method for Selective Adjustment of Exercise Apparatus," all of which are incorporated herein by reference.

BACKGROUND OF THE INVENTION

1. The Field of the Invention

The present invention relates to systems and methods for enabling communication between disparate exercise devices and computer devices. More particular, the present invention relates to providing systems and methods for two-way communication between exercise devices and computer devices that typically are incapable of communicating one with another. Further, the present invention relates to enabling one or more users on one or more exercise devices to interact in a competitive environment.

2. The Relevant Technology

At health clubs, members are taught correct techniques for using exercise equipment and performing exercises in group settings. By so doing, members are less likely to receive an exercise related injury, while exercising in a synergistic environment where group members derive encouragement and motivation from each other. Initially, only group aerobic classes were available to members of the health club. More recently, however, group workout approaches have been extended to classes that use exercise equipment or devices. For example, "Spinning Classes" are available in which each participant operates his or her own stationery exercise cycle in a group setting with a coach or instructor leading the group through a prescribed program or routine. Similar instructional classes are available at health clubs that use other types of exercise equipment or devices.

One of the primary disadvantages of group training is that such training is typically available only at health club and therefore it is not as convenient as exercising in the privacy and comfort of one's own home. Consumers are purchasing home exercise devices in record quantities in an attempt to conveniently improve their health and physical conditioning. However, ownership of a home exercise device requires the owner to maintain and/or repair the device, as necessary, and typically eliminates access to the synergistic environment of the health club and the expertise of personal trainers or instructors.

Some efforts have been made in the prior art to introduce a level of "interactivity" into home exercise equipment or devices. For example, U.S. Pat. No. 5,489,249 discloses a video exercise control system in which a videocassette recorder (VCR) or similar device is coupled, via a hard wired connection, to an exercise machine, such as a treadmill. As an individual exercises on the treadmill, the VCR in synchronization with a prerecorded audio/video presentation controls the speed and incline of the treadmill.

In U.S. Pat. No. 5,645,509, entitled "Remote Exercise Control System" that is incorporated herein by reference, disclosed a system in which an exercise device, such as a treadmill, remotely communicates via a communications module with an evaluation module located at a remote location. Signals indicative of the operating parameters of the treadmill are transmitted from the treadmill to the evaluation module, and control signals are transmitted from the remote evaluation module for controlling the operating parameters of the treadmill.

Another example of an exercise device that provides a user with some interactivity is disclosed in U.S. Pat. No. 5,888,172. The exercise device disclosed in U.S. Pat. No. 5,888,172 is coupled, via a hard-wired connection, to a video game device. The operating parameters of the exercise device are used as inputs to the video game controller, which then produces a video display based on the inputs received. While these approaches exist, they nevertheless fail to provide many desirable benefits of group exercise.

Consumers purchasing home exercise equipment for convenience are unable to enjoy many benefits of group exercises. For example, the consumers of home exercise equipment typically face challenges of understanding proper use of the equipment, of developing an exercise routine, of maintaining motivation to use the equipment on a consistent and ongoing basis, and of providing necessary maintenance and repair to the equipment. It would be a definite improvement in the art of home exercise equipment to provide the desirable benefits of group exercise in the convenience of a home setting.

BRIEF SUMMARY OF THE INVENTION

The present invention relates to systems and methods for providing two-way communication between exercise devices and computer devices. More particular, the present invention relates to translating data between different protocol formats to enable two-way communication between a computer device and an exercise device. Further, the present invention relates to enabling one or more users on one or more exercise devices to interact in a competitive environment.

In one embodiment, an implementation of the present invention takes place in association with an exercise device and a computer device. One example of such an exercise device is a treadmill, although a variety of different exercise devices may be employed, such as exercise cycles, Nordic style ski exercise devices, rowers, steppers, hikers, climbers, elliptical or striding exercise devices, incline trainers, weight systems, and any other motorized device or any other device that utilizes motors, solenoids, or any other electrically driven actuators to control one or more operating parameter of the exercise device.

According to one aspect of the invention, a computer device and a treadmill or other exercise device communicate one with another through a translator device. The treadmill allows a user to participate in an exercise program, whether such program is developed by the user, downloaded from a computer device local or remote from the treadmill, a combination thereof, and the like. The treadmill gathers device data and/or user data that are preserved in internal memory of the treadmill. Examples of device data include information relating to speed, resistance, incline, time, temperature, and other similar operating parameters. Examples of user data include information relating to a user's age, weight, height, current pulse rate, and other information specific to a user.

The data gathered by the treadmill is accessible by the computer device through a communication line connection and the translator device. The translator device is configured to translate the data between the protocol format of the computer device and the protocol format of the exercise device. Similarly, the treadmill may access data from the computer device, such as an exercise program stored at the computer device, through a similar exchange of data between the treadmill and computer device that is sent through the translator device.

As an exercise device and a computer device typically employ communication protocols with differing formats, the translator device enables the exchange of data between the devices. By way of example, the computer device transmits a request using a computer communication protocol, illustratively the recommended standard-232 (RS-232) protocol, to obtain data gathered by the treadmill. The translator device receives a request that is formatted in accordance with the computer communication protocol and translates the request into a request formatted in accordance with an exercise communication protocol, illustratively an $I^2C$ protocol, understood by the treadmill. In response, the treadmill transmits the response that is formatted in accordance with the exercise communication protocol that corresponds to the requested data. The translator device receives the response and translates the response into a response that is formatted in accordance with the computer communication protocol. As such, two-way communication between the computer device and treadmill is enabled.

According to another exemplary embodiment of the present invention, the treadmill can include all or a portion of the functionality of the translator device internal to the treadmill. For example, a processor included within the treadmill can directly format data indicative of one or more measurable parameters of the treadmill or a user exercising thereupon into a format in accordance with the computer communication protocol, such as RS-232 protocol. The treadmill can achieve this without first preparing the data for delivery using an exercise communication protocol. Consequently, the treadmill can directly communicate with the computer device via a communication line connection that accommodates data formatted in accordance with a computer communication protocol.

Two-way communication between an exercise device and a computer device provides a user of the exercise device and the computer device with the capabilities to perform various activities. Illustratively, a user of the computer device can perform a diagnostic check on the exercise device. Upon encountering a diagnostic error in the exercise device, the error may be repaired or reprogrammed remotely without the use of a technician at the exercise device. Another activity includes defining internal parameters of the exercise device upon installation of updated or new software or components.

Another activity includes allowing the computer system to monitor the status of a user, such as the user's current pulse rate, to maintain an appropriate workout for the user and/or to prevent the user from entering into an unhealthy or hazardous pulse rate. Another activity includes controlling the exercise device and/or providing instructional direction and/or encouragement relating to a particular exercise routine.

Another activity allows the computer system to monitor and optionally regulate the amount of resistance experienced by a user of the exercise device.

Communication between the exercise device and the computer device enables a user of an exercise device to compete with and/or otherwise interact with another user on either a real time or a delayed time basis. For example, a first user on or at a first exercise device at a first location competes against a second user on or at a second exercise device at a second location, even when the locations are in separate cities, states or even countries.

The first user uses a first computer device to access a server across a network to schedule a race with the second user, which uses a second computer device to access the server across the network to schedule the race with the first user. Before a start time of the race, the users begin exercising on each respective exercise device. The race begins while the users are exercising and the computer devices control an operating parameter of the exercise devices to simulate the layout or terrain of the race. When the exercise devices are treadmills, for example, the race layout is simulated by the computer system controlling or regulating the incline of the tread base of each treadmill to simulate running uphill or on a flat surface. Each exercise device and/or computer device monitors a user's performance to determine distance traveled by the user with respect to the start time of the race. The distance traveled in the race corresponds to the distance traveled on the treadmill belt. During the race, each user is able to independently set and modify the speed of the belt.

The position of each user is communicated across the network and updated throughout the race to allow for a display at each location. In one implementation, the network is a wide area network ("WAN"), such as the Internet, that allows users to compete while exercising in their own homes on home fitness equipment. The exercise device, with an incorporated computer device, or a separate computer device, performs the monitoring, tracking and/or controlling of an exercise device. The data indicative of such monitoring, tracking and/or controlling of an exercise device is communicated to the server, which processes user performance from the various computer devices and communicates the position of each user in the race to the computer devices.

Once the race ends, each computer device or client uploads the results of the race corresponding to one user or participant, relative to the start time of that user or participant, so that the server may process the results of the virtual race. Meanwhile, the users experience a cool down and are notified of the results, including the winner and the order of completion of the race, once the official results are processed by the server and communicated across the network. As such, in an implementation where the computer devices are connected to a WAN, implementation of the present invention may be performed regardless of network latency since the tracking and monitoring is performed on the client side and the processing is performed on the server side.

While the example above refers to two users racing against each other at the same time, implementations of the present invention embrace a variety of scenarios. For example, a user may race against stored races by that user or other users, against virtual users, or against a large number of other virtual and/or live users. Alternatively or additionally, users may compete at different times, such as one user participating in the morning of a first day and another user participating in the afternoon of a second day. Further, users can compete one different exercise devices, on the same exercise device one after another, combinations thereof, or the like. Once all of the users have completed the race, the exercise device and/or separate computer device uploads the race data from each user to a server. The server processes the data and notifies all users of the winner and optionally the order in which the users finished the virtual race.

Additional features and advantages of the invention will be set forth in the description which follows, and in part will be obvious from the description, or may be learned by the practice of the invention. The features and advantages of the invention may be realized and obtained through the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
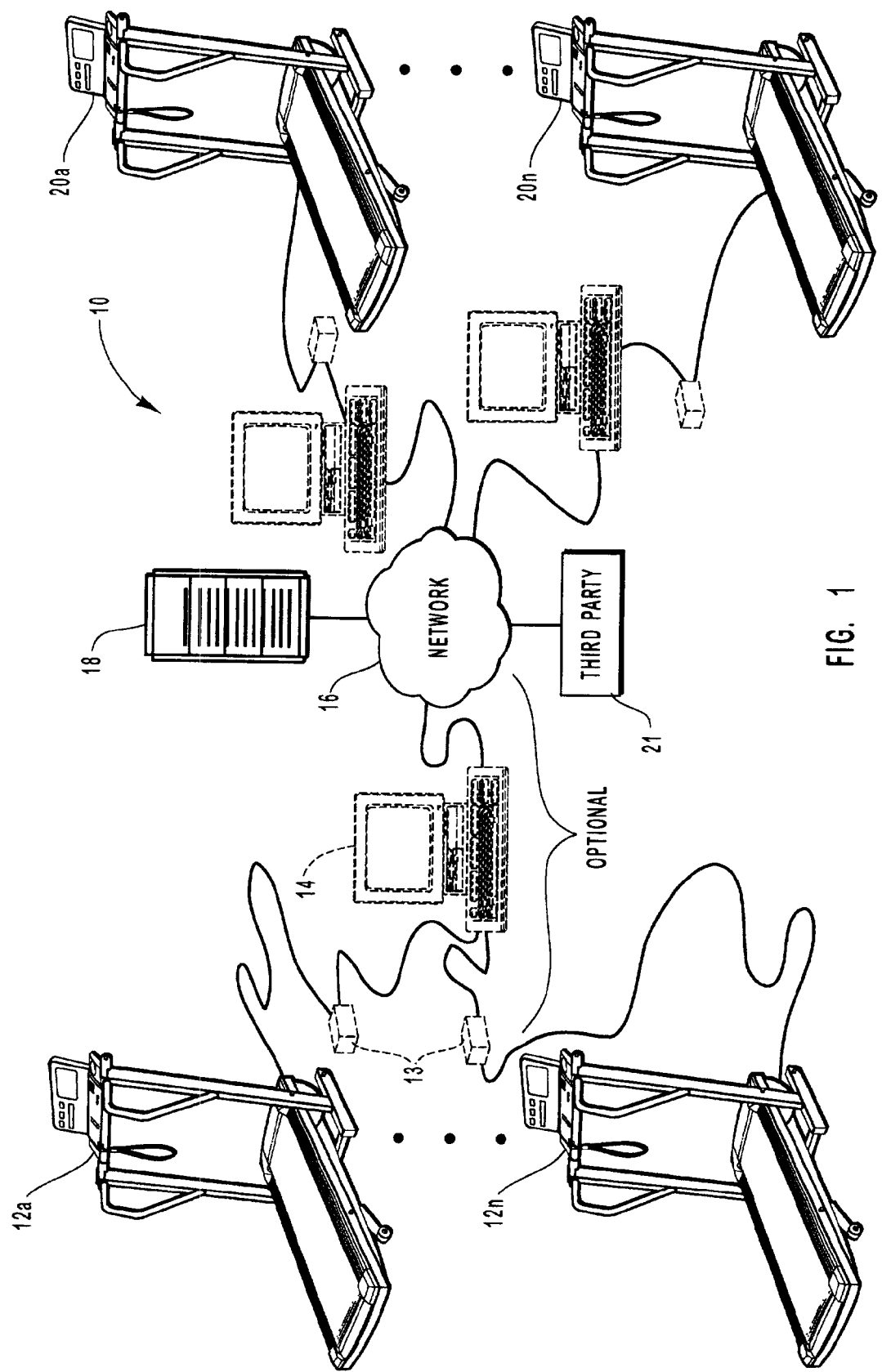
FIG. 1 is a schematic representation of an exemplary system configuration in accordance with the present invention.

The present invention relates to systems and methods for providing two-way communication between exercise devices and computer devices. Embodiments of the present invention facilitate direct communication between an exercise device and a computer device in a simple and efficient manner. Further, embodiments of the present invention relate to controlling the delivery of differently formatted data between various computer devices and exercise devices. Illustratively, the present invention relates to translating data formatted for delivery in accordance with, using, or by a computer communication protocol to data formatted for delivery in accordance with, using, or by an exercise communication protocol. Therefore, the present invention relates to enabling an exercise device to communicate with a computer device by translating data formatted for delivery in accordance with, using, or by a computer communication protocol to data formatted for delivery in accordance with, using, or by an exercise communication protocol, or vice versa.

Additionally, the present invention relates to systems and methods for enabling users utilizing an exercise device to compete in a virtual race. More particular, the present invention relates to enabling one or more users on one or more exercise devices to interact in a competitive environment, regardless of network latency and of when the users participated in the virtual race.

As discussed herein, reference is made to an exercise device. Although reference will be made to one implementation of the present invention as relates to a treadmill, it can be understood that other implementation of the present invention can be included within other exercise devices. Consequently, the term "exercise device" shall be interpreted broadly to include any type of device that takes the form of a machine or equipment that is used by an individual for performance of fitness or exercise programs, regimes, or activities. These exercise devices can include, but not limited to, treadmills, exercise cycles, Nordic style ski exercise devices, rowers, steppers, hikers, climbers, elliptical or striding exercise devices, incline trainers, weight systems, and any other motorized device or any other device that utilizes motors, solenoids, or any other electrically driven actuators to control one or more operating parameter of the device. These operating parameters include, but are not limited to, speed, resistance, incline, time, temperature, or other similar operating parameters of the exercise device.

To simplify the description of the various aspects of the present invention, the following disclosure of the present invention is grouped into various subheadings, namely "Exemplary System Configuration" and "Two-Way Communication Translation," each including multiple sub-subheadings. The use of these headings is for convenience of the reader only and is not to be construed as limiting in any sense to the scope of the present invention.

Exemplary System Configuration

Depicted in FIG. 1 is a representation of one illustrative system, designated by reference numeral 10, that may incorporate the novel features of the present invention. This system 10 includes various devices, hardware and software modules, and the like that may be remotely accessed and controlled in a real-time manner. Although this is one embodiment of an exemplary system, other systems can be identified by those skilled in the art, such as but not limited to those systems, whether in whole or in part, described in U.S. patent application Ser. Nos. 09/641,600, 09/641,220, 09/641,627, 09/349,608, and 09/496,560, all of which are incorporated herein in their entirety by this reference.

As shown, one or more exercise devices, such as treadmills 12a–12n, communicate data with a communication system 18, one or more treadmills 20a–20n, or a third party 21 via one or more translators or translator devices 13 and one or more computer devices 14. Alternatively, each exercise device can communicate data with computer device 14 through translator device 13, with computer device 14 optionally communicating with communication system 18, treadmills 20a–20n, and/or third party 21. Further, each exercise device can communicate data directly with computer device 14 without the aid of translator device 13.

Each translator device 13 and/or computer device 14 communicates with a network 16 configured to enable communication of the various hardware and software modules and devices of the present invention. Network 16, therefore, can be a local area network (LAN), a wide area network (WAN), a wireless network, a packetized network, a real-time network, and the like.

Communication system 18 may assist with the communication between the different modules, hardware devices, or exercise devices or mechanism of system 10. Optionally, communication system 18 acts as a data store for data deliverable to and/or received from treadmills 12a–12n, 20a–20n, third party 21, translator device 13, and computer device 14. The functionality of communication system 18 is more fully described in U.S. patent application Ser. Nos. 09/641,600, 09/641,220, and 09/641,627.

The following discussion will be directed to only a single treadmill 12 and a single treadmill 20, however, it may be appreciated that a similar discussion may be made for the illustrated configuration that includes multiple treadmills 12a–12n, 20a–20n. Similarly, although each of the elements of system 10 are shown separated one from another, it may be appreciated by one skilled in the art that the hardware and/or software modules and elements of the present invention may be incorporated together. For example, the functionality and/or the structure of translator device 13 and/or computer device 14 may be excluded, or partially or completely incorporated within respective exercises devices or mechanisms, such as treadmill 12 or treadmill 20. Similarly, the functionality, the structure, the hardware and/or the software elements of the communication system 18 may be partially or completely incorporated within a treadmill.

Generally, system 10 enables data, such as motivational content and one or more control signals, to be transmitted between one or more translator devices 13, computer device 14, treadmills 12a–12n, 20a–20n, communication system 18, and third party 21. In one configuration, such data includes data indicative of any measurable parameter of the exercise device, such as but not limited to, speed, resistance, incline, time, temperature, or other similar operating parameters of the exercise devices. In still another configuration, the data is indicative of any measurable parameter of the user of the exercise device, such as but not limited to, heart rate, blood pressure, weight, or the like. The data can be formatted in accordance with, by, or using either a computer communication protocol or an exercise communication protocol. Further, the data that is sent can be considered as a protocol, whether a computer protocol or an exercise protocol. In another configuration, the data is so formatted to initiate a diagnostic analysis of computer device 14, translator device 13, treadmill 12a–12n, 20a–20n, communication system 18 or third party 21 and return resulting status information to one or more of the above.

Additionally, the data can optionally include exercise programming with control signals to be transmitted from one module, component, or device of system 10 to another. As disclosed in U.S. Pat. Serial No. 09/349,608 entitled "Systems and Methods for Providing an Improved Exercise Device with Motivational Programming," which is incorporated herein by reference, the programing includes motivational content and/or one or more control signals that control one or more operating parameters of the exercise device. The control signals may be synchronized with the motivational content and designed to control one or more operating parameters of the exercise device, such as the speed, incline, difficulty of exercise program, time, distance, and the like of an exercise program performed on the exercise device.

As used herein, the term "motivational content" is used to broadly refer to any audio material, including dialog, narration, sound effects, and/or music, either alone or in combination with video material. In one embodiment of the present invention, the motivational content is stored in communication system 18 and includes an audio/video presentation of a personal trainer and others engaged in a series of exercises of varying difficulty. In another embodiment of the present invention, the motivational content is a live-on-live, real-time exercise program presented by one or more personal trainers that is either specific to one particular user or alternatively broadcast or optionally "webcast" to any user that it may access communication system 18. In still yet another embodiment, the programming includes an exercise profile of the intensity of various exercise criteria, such as but limited to, speed, incline, or resistance of the exercise device, that is displayed continually or periodically to the user during the performance of the programming. In still yet another embodiment of the present invention, the user controls the period of when the exercise profile appears. One skilled in the art may appreciate that various other configurations of programming are applicable.

FIGS. 2–5 and the corresponding discussion are intended to provide a general description of a portion of the suitable operating environment illustrated in FIG. 1. Although not required, the invention will be described in the general context of a system that includes an exercise device, a translator device, and a computer device. Those skilled in the art, however, will appreciate that embodiments of the present invention may be practiced in a variety of different system configurations that include different exercise devices, translator devices, and/or computer devices.

Figure 2:
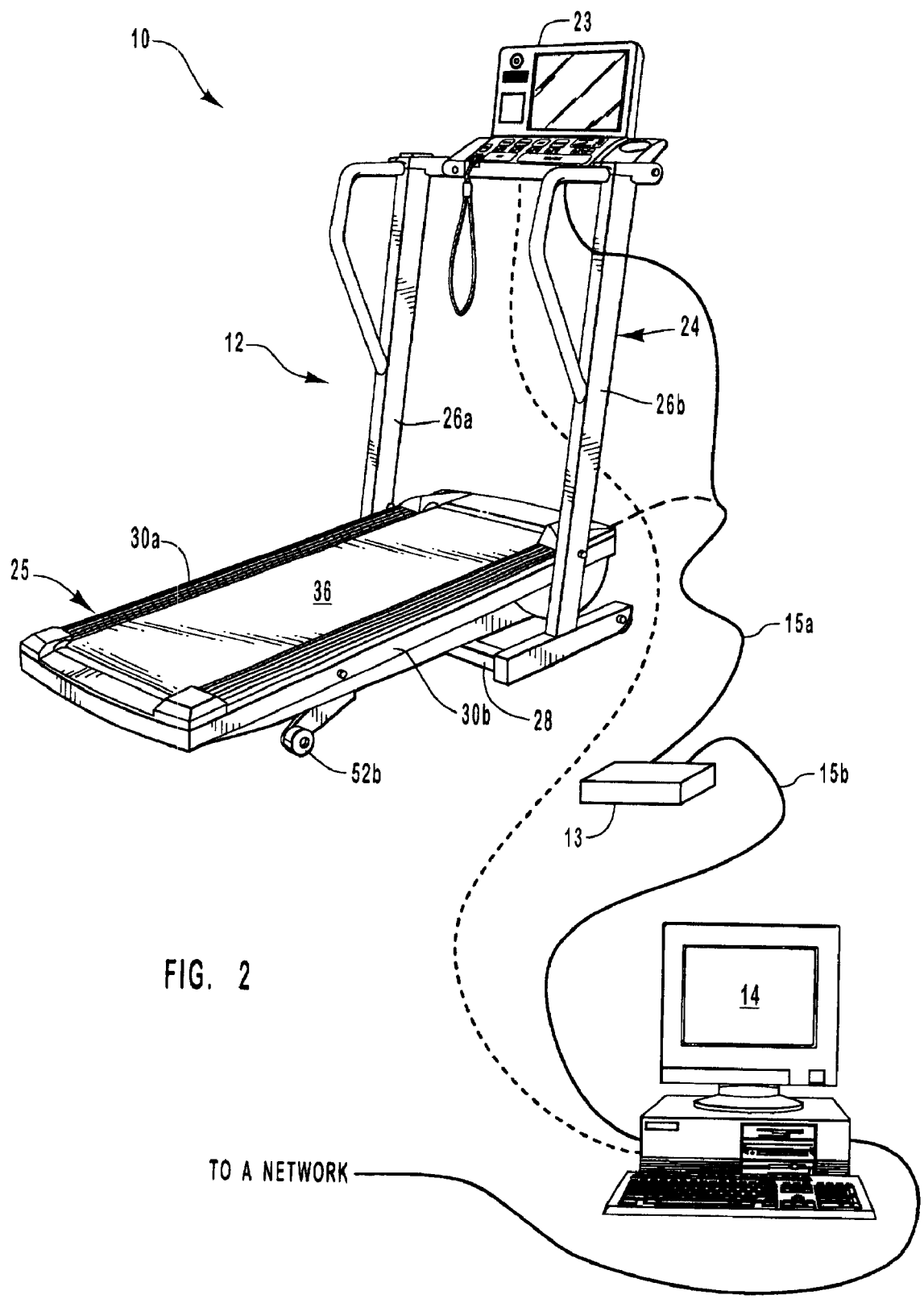
FIG. 2 is a perspective illustration of an exemplary system configuration of the present invention of FIG. 1, wherein a computer device and translator device are connected to an exercise device.

Referring to FIG. 2, an exemplary system configuration is illustrated that provides an exemplary environment for one implementation of the present invention. In FIG. 2, system 10 is provided that includes an exercise device 12, a computer device 14, and a translator device 13. Although not required, exercise device 12 is illustrated as a motorized, reorienting treadmill that is capable of receiving data from and delivering data to computer device 14 through translator device 13. Communication between exercise device 12 and computer device 14 is transmitted across a transmission medium, illustrated in FIG. 2 as cables 15a and 15b that respectively couple exercise device 12 to translator device 13 and translator device 13 to computer device 14. In other embodiments, exercise device 12 communicates directly with computer device 14 through the transmission medium, without an external translator device 13, as illustrated by the dotted line extending between computer device 14 and exercise device 12.

Embodiments of the present invention embrace the use of other transmission mediums for delivering and receiving data between exercise device 12 and computer device 14, including a wireless communication system, a radio frequency (RF) communication system, fiber-optic communication system, any electromagnetic communication system, and other communication systems capable of being used to transmit data as known by one skilled in the art in light of the teaching contained herein.

Although not required, FIG. 2 illustrates computer device 14 and translator device 13 as being external to exercise device 12. Other embodiments of the present invention embrace the functionality and/or structure of (i) computer device 14 and/or translator device 13 being internal to exercise device 12, (ii) translator device 13 being internal to computer device 14, (iii) translator device 13 being internal to exercise device 12, (iv) combinations thereof, and the like. In still another configuration, exercise device 12 is configured to directly communicate with computer device 14 without utilizing the functionality and/or structure of translator device 13.

A. Exemplary Exercise Device

The following discussion is intended to provide a description of an exemplary exercise device, illustrated in FIG. 2 as treadmill 12. In one embodiment, treadmill 12 includes a control panel 23 supported on a generally upright support structure 24 and a tread base 25. The illustrative upright support structure 24 includes two side members 26a, 26b that are coupled by way of one or more cross members 28. Side members 26a, 26b and cross members 28 can have various configurations and may be fabricated from various materials so long as they are capable of supporting control panel 23 and tread base 25. For example, the elements of upright support structure 24 can be fabricated from metals, plastics, natural materials, composites, combinations thereof, and the like.

The tread base 25 can be placed in one of a variety of positions. For example, FIG. 2 illustrates tread base 25 in a downward position that allows an individual to exercise thereon. While in the downward position, tread base 25 can be selectively angled with respect to the surface upon which treadmill 12 rests to provide further resistance to the individual exercising thereupon.

Figure 3:
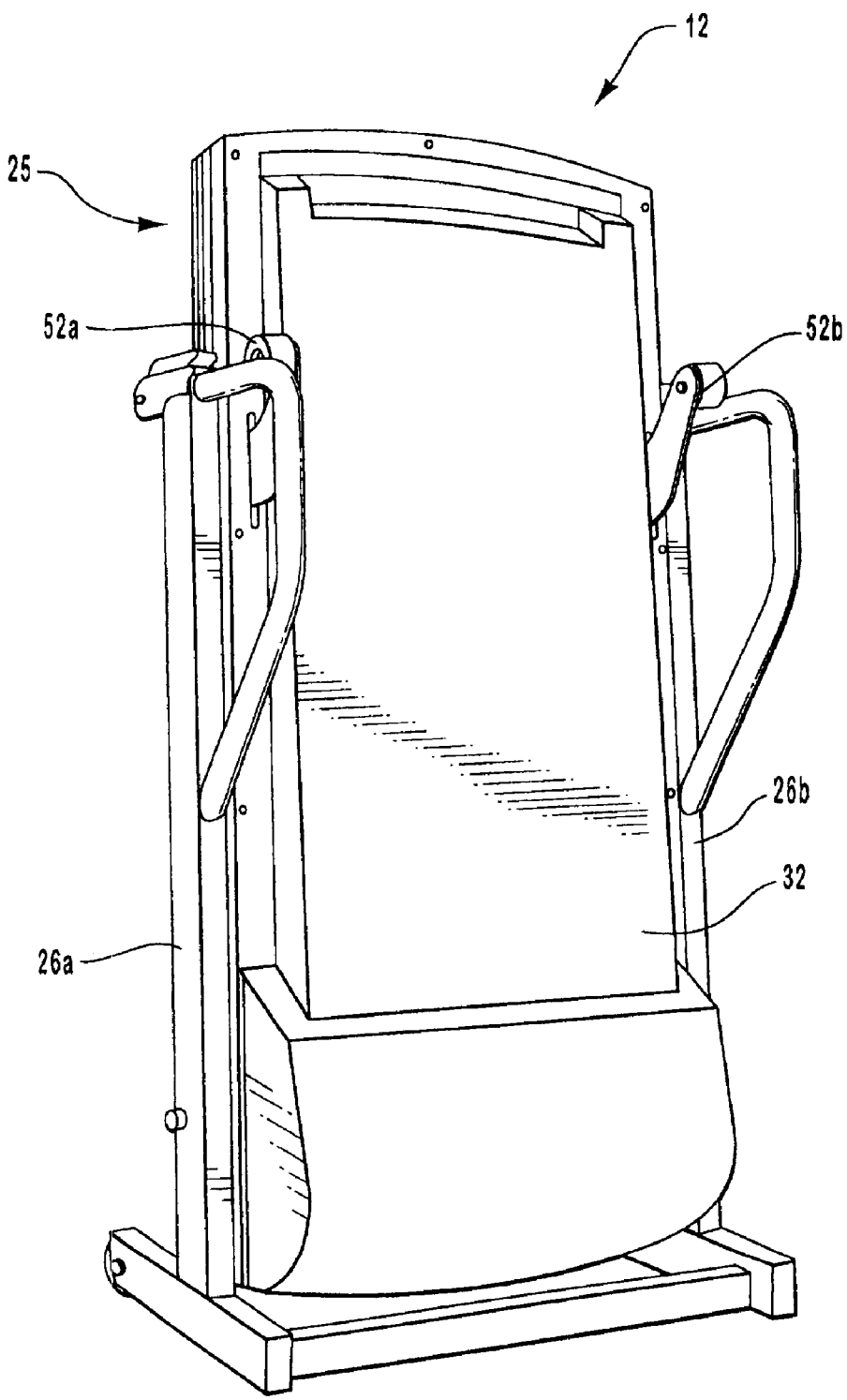
FIG. 3 is a perspective illustration of the exercise device of FIG. 2 with the tread base positioned in an upward position for storage.
Figure 4:
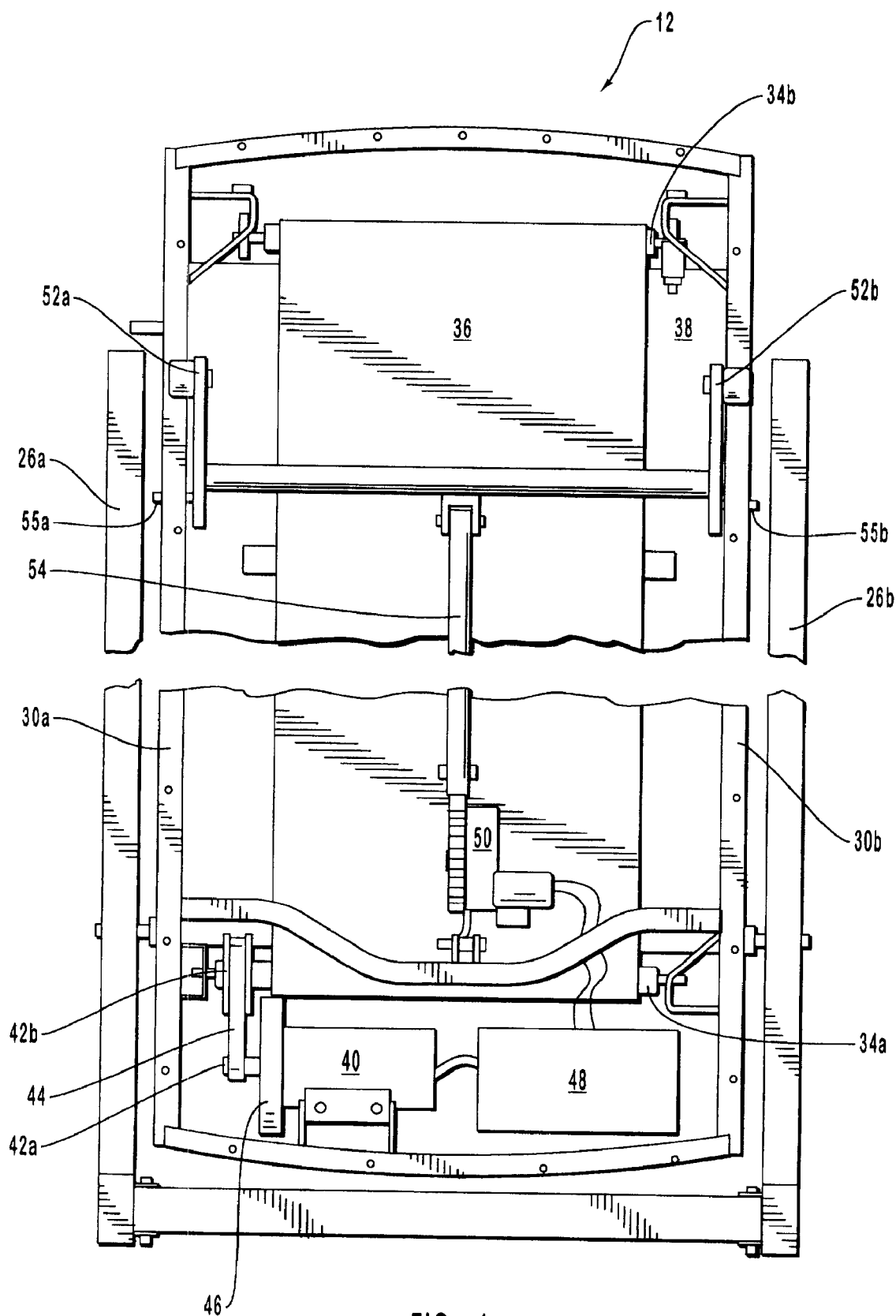
FIG. 4 is a partial plan view of portions of the exercise device of FIG. 2 with the tread base oriented in the upward position.

As illustrated in FIGS. 3 and 4, tread base 25 can be placed in an upward position for storage. To aid with the description of treadmill 12, FIG. 4 illustrates a partial view of portions of treadmill 12 with tread base 25 in an upward position and with a bottom cover 32 of FIG. 3 removed so as to reveal some of the internal components of treadmill 12.

Referring to FIG. 4, tread base 25 typically includes a pair of side rails 30a, 30b each having a front portion proximal to and a rear portion distal from upright support structure 24 (FIG. 1) when tread base 25 is in the downward position. A proximal pulley 34a (FIG. 3) and a distal pulley 34b, with relation to the support structure 24, are disposed between and supported by side rails 30a, 30b while a continuous belt 36 extends between and around proximal pulley 34a and distal pulley 34b. Belt 36 is an example of a movable element that enables the performance of an exercise by a user when the exercise device is a treadmill. Pulleys 34 and belt 36 may have various configurations and may be fabricated from various materials, as known by one skilled in the art.

A deck 38 supports the upper run of belt 36 and supports an exercising individual resting upon belt 36; the individual is not shown. Deck 38 is fabricated from various types of materials that allow deck 38 to support belt 36 and a user exercising thereon. For instance, deck 38 can be fabricated from wood, plastics, metals, natural materials, composite materials, combinations thereof, and the like.

As shown, proximal pulley 34a is mechanically coupled to an electric tread drive motor 40 by way of pulleys 42a, 42b and a drive belt 44. In this illustrative embodiment, motor 40 further incorporates an inertial flywheel 46 that controls fluctuations in the rotational motion of a shaft of motor 40 during operation of treadmill 12. Motor 40 is optionally electrically coupled to a treadmill controller 48 that controls the operation of motor 40 and the speed of belt 36 in response to various inputs or other control signals. As shown, treadmill controller 48 is incorporated within tread base 25, however one skilled in the art can appreciate that treadmill controller 48 may be incorporated within control panel 23 or alternatively within computer device 14 of FIG. 2.

In addition to the ability to control and vary the speed of belt 36, treadmill 12 also permits the degree of incline of tread base 25 to be varied relative to the surface upon which tread base 25 rests. Typically, this is accomplished through use of an incline drive motor 50 (FIG. 4) that raises or lowers one end of tread base 25 relative to the other end. In the illustrated embodiment, tread base 25 includes a pair of feet 52 that are rotatably attached to the underneath portion of side rails 30. Feet 52 are mechanically coupled through a shaft 54 to incline drive motor 50, which causes feet 52 to pivot about their points 55 of pivotal attachment to side rails 30a, 30b, thereby selectively raising or lowering the distal end of tread base 25, relative to support structure 24, when the treadmill 12 is in a downward position. Motor 50 is also optionally electrically coupled to and controlled by the treadmill controller 48.

Figure 5:
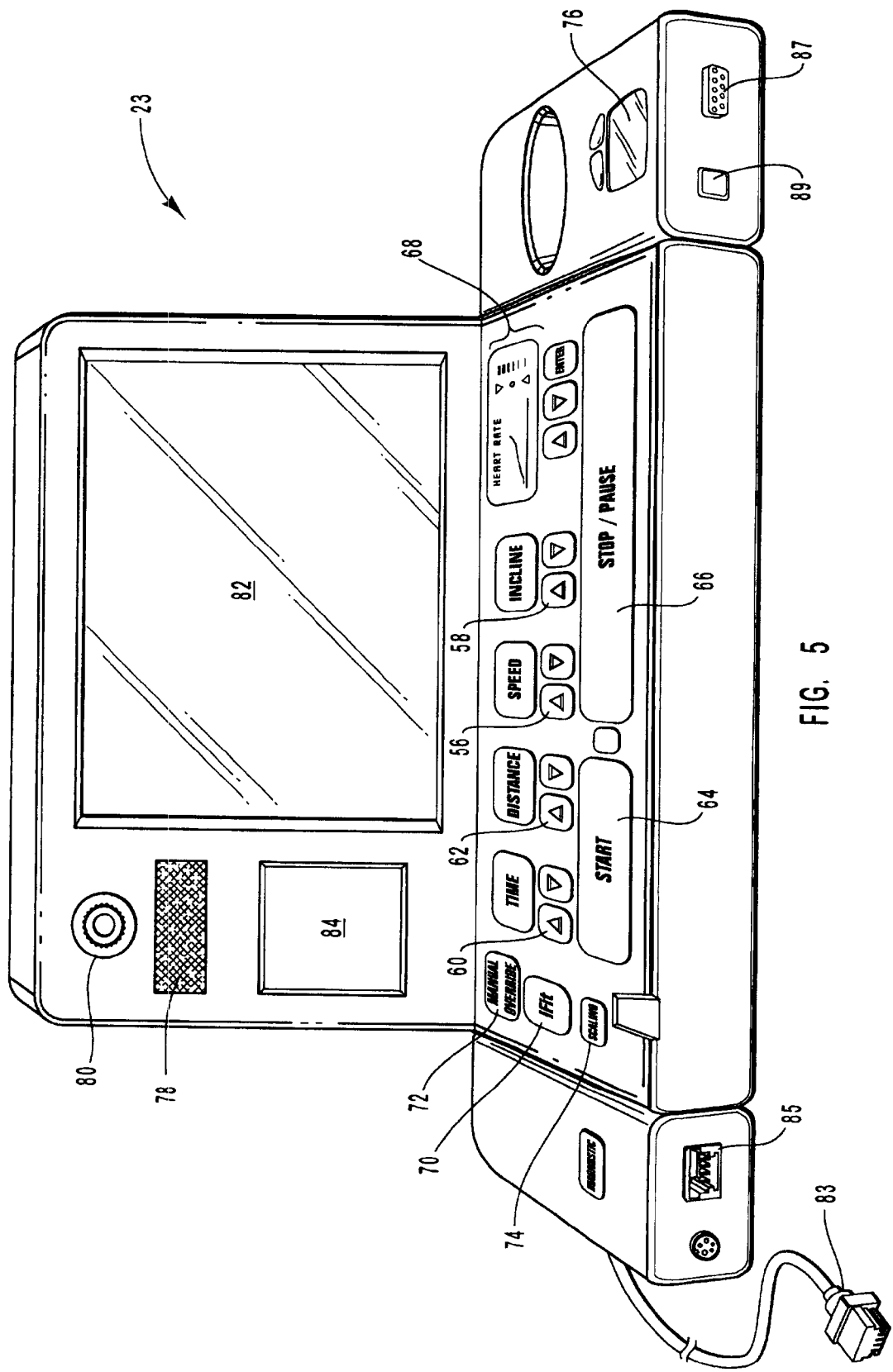
FIG. 5 is a perspective illustration of a control panel of the exercise device of FIG. 2.

Treadmill 12 includes a control panel 23 attached to upright support structure 24. In one embodiment, as illustrated in FIG. 5, control panel 23 includes one or more input device and one or more output devices that provide an interface through which a user can input and receive information and data. Examples of input devices include, but are not limited to, speed controls 56, incline controls 58, time controls 60, distance controls 62, a start button 64, a stop/pause button 66, heart rate controls 68, an iFit.com button 70, a manual override button 72, a scaling control 74, a mouse 76, a microphone 78, a camera 80, and the like. Examples of output devices include video display 82 that provides video output, a speaker 84 that provides audio output, a plurality of visual displays or indicators for each of the speed controls 56, incline controls 58, time controls 60, distance controls 62, start button 64, stop/pause button 66, heart rate controls 68, iFit.com button 70, manual override button 72, scaling control 74, and the like.

According to one illustrative embodiment, each button includes a light that becomes illuminated when the button is activated and darkens when deactivated, or vice versa. Further, each control can include an liquid crystal display (LCD) that provides a visual representation of the operating parameter changed through manipulation of the control, i.e., by changing the speed, incline, distance, etc. the LCD displays different values for the speed, incline, distance, etc. It may be appreciated that each of the above-recited devices may be embodied in a variety of different manners to perform their commonly utilized function, and may take the form of one or more switches, rheostats, potentiometers, touch sensitive controls, voice activated controllers, and the like.

In addition to the above input and output device, control panel 23 can include input and output devices that enable control panel 23 and hence treadmill 12 to communicate with translator device 13 and/or computer device 14. As shown, control panel 23 optionally includes a hardwire connection 83 configured with an I²C adaptor for allowing communication to translator device 13. Alternatively, control panel 23 can optionally include an I²C port 85 that is adapted to cooperate with an I²C adaptor to facilitate communication between treadmill 12 and translator device 13.

As illustrated, control panel 23 can optionally include an input/output port 87, such as an RS-232 port, that enables control panel 23 and treadmill 12 to directly communicate with computer device 14. Similarly, control panel 23 includes a wireless port 89 that enables control panel 23 and treadmill 12 to communicate with translator 13 and/or computer device 14 using one of a variety of different electromagnetic radiation transmission mediums, such as but not limited to, radio frequency, infra-red, microwave, or the like transmission mediums.

Figure 6:
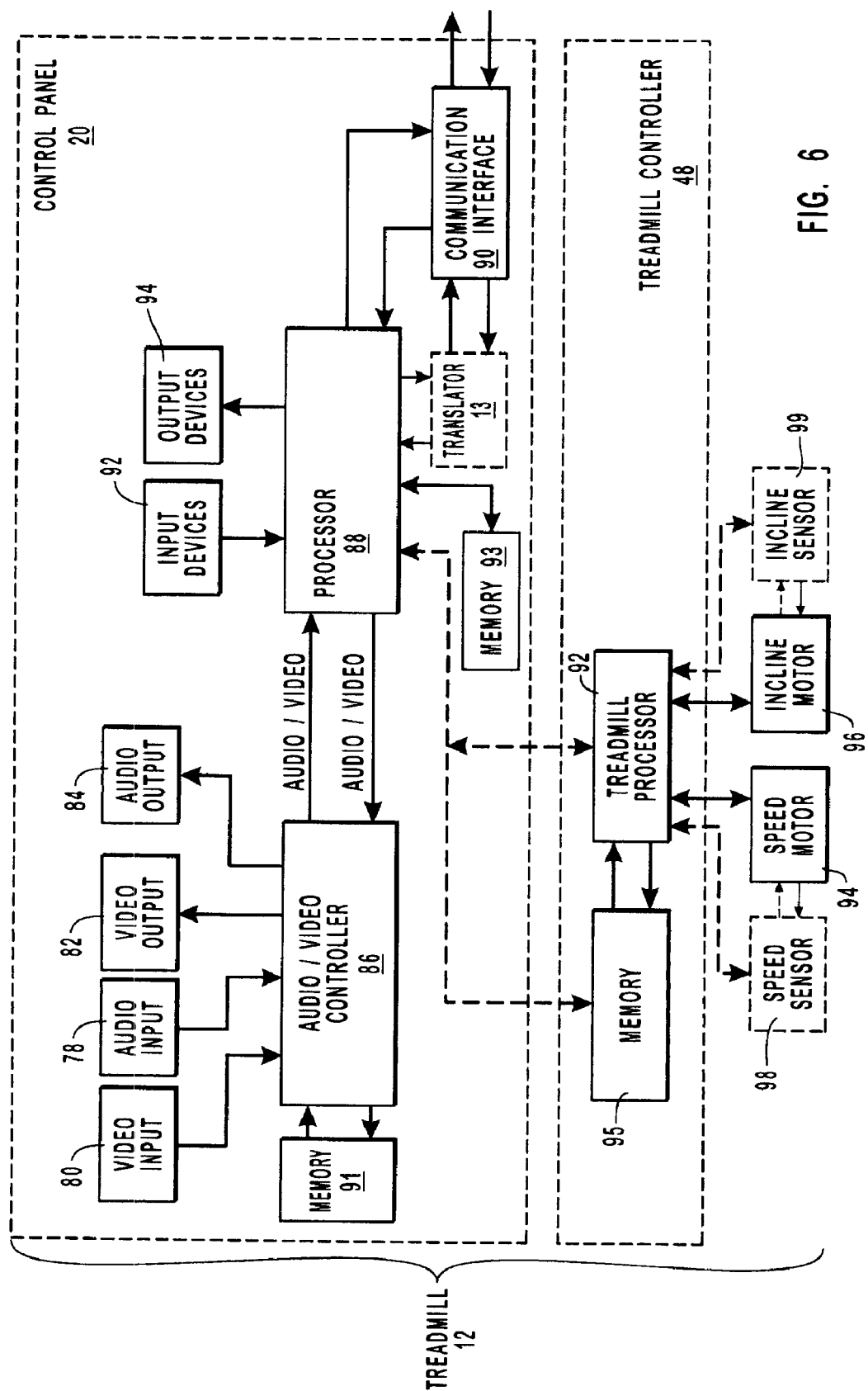
FIG. 6 is an exemplary schematic representation of the exercise device of FIG. 2.

With reference to FIG. 6, an exemplary functional block diagram of treadmill 12 is illustrated. In FIG. 5, control panel 23 communicates with computer device 14 through translator device 13, and optionally with network 16, communication system 18, and/or other treadmills 20a–20n, computer devices 14, and translator devices 13 (FIG. 1). Therefore, control panel 23, or the various hardware and/or software modules and components deliver data indicative of any measurable parameter of the exercise device and/or the user of the device to communication system 18, and/or other treadmills 20a–20n, computer devices 14, and translator devices 13 (FIG. 1) and receive data from other translator devices 13, computer devices 14, and communication system 18. Any individual module, component, exercise device, or the like forming part of system 10 can initiate the bi-directional communication between the various portions of system 10.

When the functionality of translator device 13 is incorporated within control panel 23, such as illustrated by translator device 13 depicted in dotted lines, control panel 23 bi-directionally communicates with computer devices 14, translator devices 13, communication system 18, and/or third party 21. Similarly, when the functionality of computer device 14 is incorporated within control panel 23, control panel 23 bi-directionally communicates with network 16, communication system 18, and/or other treadmills 20a–20n, computer devices 14, and translator devices 13 (FIG. 1).

Although reference is made to control panel 23 communicating with various computer devices, translator devices, communication systems, and third parties, it can be understood that generally the exercise device bi-directionally communicates with such computer devices, translator devices, communication systems, and/or third parties. Therefore, the functionality and related hardware and/or software modules and components need not be only included in the control panel, rather, such functionality and related hardware and/or software modules and components can be included within any module, component, or the like of the exercise device.

As shown in FIG. 6, control panel 23 includes an audio input device 78, such as a microphone, for gathering audio signals and a video input device 80, such as a video camera for gathering video signals. The audio and video receivers need not be incorporated within control panel 23, but can be separate therefrom while communicating with exercise device 12 and/or control panel 23 using a communication line connection as described herein or known by those skilled in the art. Further, treadmill 12 need not include any audio or video input devices or audio or video output devices. Similarly, treadmill 12 can include any combination of audio devices or video devices.

The audio and/or video signals from audio input device 78 and video input device 80 are delivered to an audio/video controller 86 that is configured to manipulate the audio and video signals in preparation for transmission to a processor 88. The audio/video controller 86 can store all or a portion of the retrieved signals in a memory 91 before delivering the signals to processor 88. In this manner, the signals can be buffered as needed. Memory 91 can have various forms as known to one skilled in the art, such as but not limited to, volatile, non-volatile, persistent, virtual, physical, or the like.

The processor 88 acts as the central hub of treadmill 12 and controls the operation of treadmill 12. Accordingly, processor 88 is capable of sending and receiving signals through a communication interface 90 to translator device 13 and/or directly to computer device 14 (FIG. 2). Additionally, processor 88 is capable of retrieving data indicative of any measurable parameter of treadmill 12 and/or the user exercising using treadmill 12 and reformatting the data into computer data deliverable in accordance with or using a computer communication protocol. Alternatively, processor 88 is capable of retrieving data indicative of any measurable parameter of treadmill 12 and/or the user exercising using treadmill 12 and reformatting the data into exercise data deliverable in accordance with or using an exercise communication protocol. Therefore, processor 88 can control whether treadmill 12 can communicate directly with computer device 14 or whether translator device 13 facilitates communication between computer device 14 and treadmill 12.

Further, processor 88, through communication interface 90, can deliver data indicative of any measurable parameter of the exercise device or user exercising thereupon and receive control signals to change any of the one or more measurable parameters of the exercise device. Additionally, processor 88 can initiate changes in the operating parameters of treadmill 12 in accordance with control signals received through communication interface 90.

In general, therefore, processor 88 performs various operations on the signals, such as packing, encrypting, splitting, and the like. Further, processor 88 can be configured to format data indicative of any measurable parameter of treadmill 12 from treadmill controller 48 and/or any measurable parameter from the user of treadmill 12, through appropriate hardware and/or software devices and modules. The processor 88, therefore, can facilitate the delivery of such data directly to computer device 14 through communication interface 90 using a computer communication protocol, such as but not limited to RS-232 protocol. Processor 88 is one example of means for generating computer data deliverable to the computer device. Generally, the exercise device and any components or modules thereof are examples of means for generating computer data deliverable to the computer device. Similarly, processor 88 is one example of structure performing the function of means for generating exercise data deliverable to the translator device. As with the means for generating computer data, the exercise device and any components or modules thereof are examples of means for generating exercise data deliverable to the translator device. Further, processor 88, the exercise device, and any components or modules thereof are examples of structure capable of performing the function of means for generating computer data based upon the exercise data. Additionally, processor 88, the exercise device, and any component or module thereof is a structure capable of performing the function of means for generating exercise data, based upon the computer data, in accordance with an exercise communication protocol such that the exercise data is deliverable to the exercise device. Similarly, processor 88, the exercise device, and any component or module thereof is a structure capable of performing the function of means for generating computer data, based upon the exercise data, in accordance with a computer communication protocol such that the computer data is deliverable to the computer device.

Generally, communication interface 90 is one example of structure capable of performing the function of means for receiving computer data from a computer device. Further, communication interface 90 is one example of structure capable of performing the function of means for delivering the computer data to the computer device. Similarly, communication interface 90 is one example of structure capable of performing the function of means for delivering the exercise data to the exercise device. Additionally, communication interface 90 is an example of structure capable of performing the function of means for communicatively coupling the exercise device to a computer device and or receiving computer data from the computer device and means for delivering the computer data to the computer device.

The communication interface 90 and the various above-recited means can have various configurations to enable communication between treadmill 12, translator device 13, and/or computer device 14 (FIG. 2). For instance, when treadmill 12 communicates directly with computer device 14 and treadmill 12 is devoid of the functionality associated with translator device 13, communication interface 90 can take the form of an RS-232 port. Alternatively, communication interface 90 can be an RS-232 port when treadmill 12 includes the structure and/or functionality of translator device 13. In another configuration, communication interface 90 can take the form of an I²C port or a hardwire I²C connection. One skilled in the art in light of the teaching contained herein knows other configurations. For instance, communication interface 90 can be a parallel interface, a serial interface, a wireless interface, an infra-red interface, other electromagnetic signal interfaces, or the like.

In addition to receiving signals or data from audio input device 78 and video input device 80, processor 88 receives various inputs from one or more manually operated input devices 92 (e.g. manual override button 72, scaling controls 74, etc.) to vary the operating parameters of treadmill 12. Optionally, processor 88 provides the user with notification of such change in the operating parameters of treadmill 12 via output devices 94, video display 82 and/or speaker 84.

Further, processor 88 can receive data or signals indicative of any measurable parameter of treadmill 12 from a treadmill controller 48. In one embodiment, treadmill controller 48 includes memory 95 and a treadmill processor 92 that is configured to control the operation of speed motor 94 and incline motor 96, which respectively controls and inclines treadmill 12. This treadmill controller 48 optionally communicates with processor 88 and with interface 90. Such communication between control processor 88 and treadmill controller 48 is achieved through use of an I²C bus, a SPI bus, a microwire bus, a microbus, and the like with associated communication protocols. Generally, the signals or data delivered between hardware and/or software modules of the exercise device are deliverable by an exercise communication protocol.

Treadmill 12 optionally includes one or more sensors, such as belt speed sensor 98 and incline sensor 99. Each sensor gathers a particular operating parameter of treadmill 12, such as the speed of belt 36 (FIG. 3) and incline of tread base 25, such that control panel 23 presents outputs that are indicative of the present operating state of treadmill 12 at any given point in time. Treadmill 12 includes other sensors that gather various other operating parameters, such as but not limited to, maximum pulse and heart rate, average pulse and heart rate, target heart rate, length of workout session, and the like. Additionally, sensors 98 and 99, in combination with one or more other sensors, determine whether an individual is actually exercising on treadmill 12 and deliver a feedback signal to processor 88. Generally, sensors 98 and 99 are examples of means for sensing exercise data at the exercise device.

Thus, treadmill 12 is one example of an exercise device that tracks one or more measurable operating parameters of the exercise devices and optionally one or more measurable parameters of the individual, i.e., heart rate, distance traveled, blood pressure, etc. and delivers such parameters to a computer device, such as computer device 14 of FIG. 2. Consequently, treadmill 12 alone or in combination with computer device 14 and/or communication system 18 (FIG. 1) track the performance of the user exercising utilizing the exercise device, i.e., treadmill. The exchange of data may be initiated by the exercise device, by a user, by the translator device, by the computer device, or by a computer device or individual remote from the exercise device, the user, or the computer device, such as described in co-pending U.S. patent application Ser. Nos. 09/641,600, 09/641,220, and 09/641,627.

B. Exemplary Computer Device and Translator

The following discussion is intended to provide a general description of an exemplary computer device, illustrated in FIG. 1 as computer device 14, followed by a description of an exemplary translator, illustrated as translator device 13, which may be used in accordance with the present invention. Those skilled in the art will appreciate that computer device 14 and/or translator device 13 may take a variety of configurations, including personal computers, hand-held devices, multi-processor systems, microprocessor-based or programmable consumer electronics, telephones, network PCs, minicomputers, mainframe computers, and the like. Additionally, computer device 14 and/or translator device 13 may be part of a distributed computer environment where tasks are performed by local and remote processing devices that are linked (either by hardwired links, wireless links, or by a combination of hardwired or wireless links) through a communications network.

Although shown as separate devices, one skilled in the art can understand that the structure of and functionality associated with computer device 14 and/or translator device 13 can be optionally partially or completely incorporated within treadmill 12, such as within one or more processors or other components of the control panel and/or treadmill controller.

As shown in FIGS. 1 and 2, communicating with an exercise device, such as treadmill 12, optionally through translator device 13 is a computer device illustrated as computer device 14. In one embodiment of the present invention, and with reference to FIG. 6, computer device 14 is a general purpose computing device that includes a processing unit 100, computer memory 102, and computer bus 104, which couples various computer components including the computer memory 102 to the processing unit 100. The computer bus 104 may be any of several types of bus structures including a memory bus or memory controller, a peripheral bus, or a local bus using any of a variety of bus architectures.

In the illustrated embodiment, computer memory 102 includes read only memory (ROM) 106 and random access memory (RAM) 108. A basic input/output system (BIOS) 110 containing basic routines that help transfer information between elements within computer device 14, such as during start-up, may be stored in ROM 106.

The computer device 14 may also include a magnetic hard disk drive 112 for reading from and writing to a magnetic hard disk 114, a magnetic disk drive 116 for reading from or writing to a removable magnetic disk 118 and an optical disk drive 120 for reading from or writing to a removable optical disk 122 such as a CD-ROM or other optical media. The magnetic hard disk drive 112, magnetic disk drive 116, and optical disk drive 120 are respectively connected to computer bus 104 by a hard disk drive interface 124, a magnetic disk drive-interface 126, and an optical drive interface 128. The drives and their associated computer-readable media provide nonvolatile storage of computer-executable instructions, data structures, program modules, and other data for computer device 14. Although the exemplary environment described herein may employ a magnetic hard disk 114, a removable magnetic disk 118, and a removable optical disk 122, other types of computer readable media for storing data can be used, including magnetic cassettes, flash memory cards, digital video disks, Bernoulli cartridges, RAMs, ROMs, and the like.

Computer device 14, in one embodiment, further includes program code means comprising one or more program modules, including an operating system 130, one or more application programs 132, other program modules 134, and program data 136, stored in RAM 108. Optionally or additionally, program modules may be stored on hard disk 114, magnetic disk 118, optical disk 122 or ROM 106.

A user may enter commands and information into computer device 14 through a keyboard 138, a pointing device 140, or other input devices (not shown), such as but not limited to microphones, joy sticks, game pads, scanners, video cameras, potentiometers, buttons, switches, rheostats, or the like, whether such devices are incorporated within treadmill 12 and/or computer device 14. These and other input devices are often connected to processing unit 80 through a serial port interface 142 coupled to computer bus 84. Alternatively, the input devices may be connected by other interfaces, such as a parallel port, a game port, or a universal serial bus (USB), and the like. A monitor 144 or other video display device is optionally connected to computer bus 104 via an interface, such as video adapter 146. In addition to the monitor, personal computer device 14 may include other peripheral output devices (not shown), such as one or more speakers, and printers for obtaining recent statistical information regarding the user's workouts. In one embodiment, the output devices are incorporated within treadmill 12.

The computer device 14, as depicted in this illustrative embodiment, may optionally operate in a networked environment using logical connections to one or more remote computers and/or servers, such as remote computer device 148 that can represent communication system 18, third party 21, other computers 14, or other translator devices 13. Furthermore, computer device 14 may optionally communicate with treadmill 12 that incorporates an integral translator device 13 via a local area network ("LAN") 150. Optionally, the translator may be internal to computer device 14.

In another configuration, computer device 14 may communicate with another exercise device 20 and/or a remote computer device 148, such as communication system 18 and/or third party 21, via a wide area network ("WAN") 154 using at least one translator device (not shown). The translator device may be internal to computer device 14 remote computer device 148 or exercise device 20. Remote computer device 148 may optionally be internal to exercise device 20.

As illustrated, remote computer device 148 may include a memory storage device 156 and one or more associated application programs 158, which optionally may correspond, for example, to a website that enables a user at an exercise device, through the translator device, to obtain the service of a stored or personal trainer to perform programming, ask questions, download or access programming materials, surf the web, gather and send electronic mail messages ("e-mail"), listen to audio programming, view video programming, review and update user information and statistics, load user statistics, purchase exercise programming, equipment, and materials, update exercise device software and operating parameters, research exercise materials, and the like. Generally, each remote computer device 148, exercise device 152 and/or treadmill 12 may be or include the structure and perform the function of another personal computer, a server, a router, a network PC, a peer device, or other common network node, and typically includes many or all of the elements described above relative to computer device 14.

Figure 7:
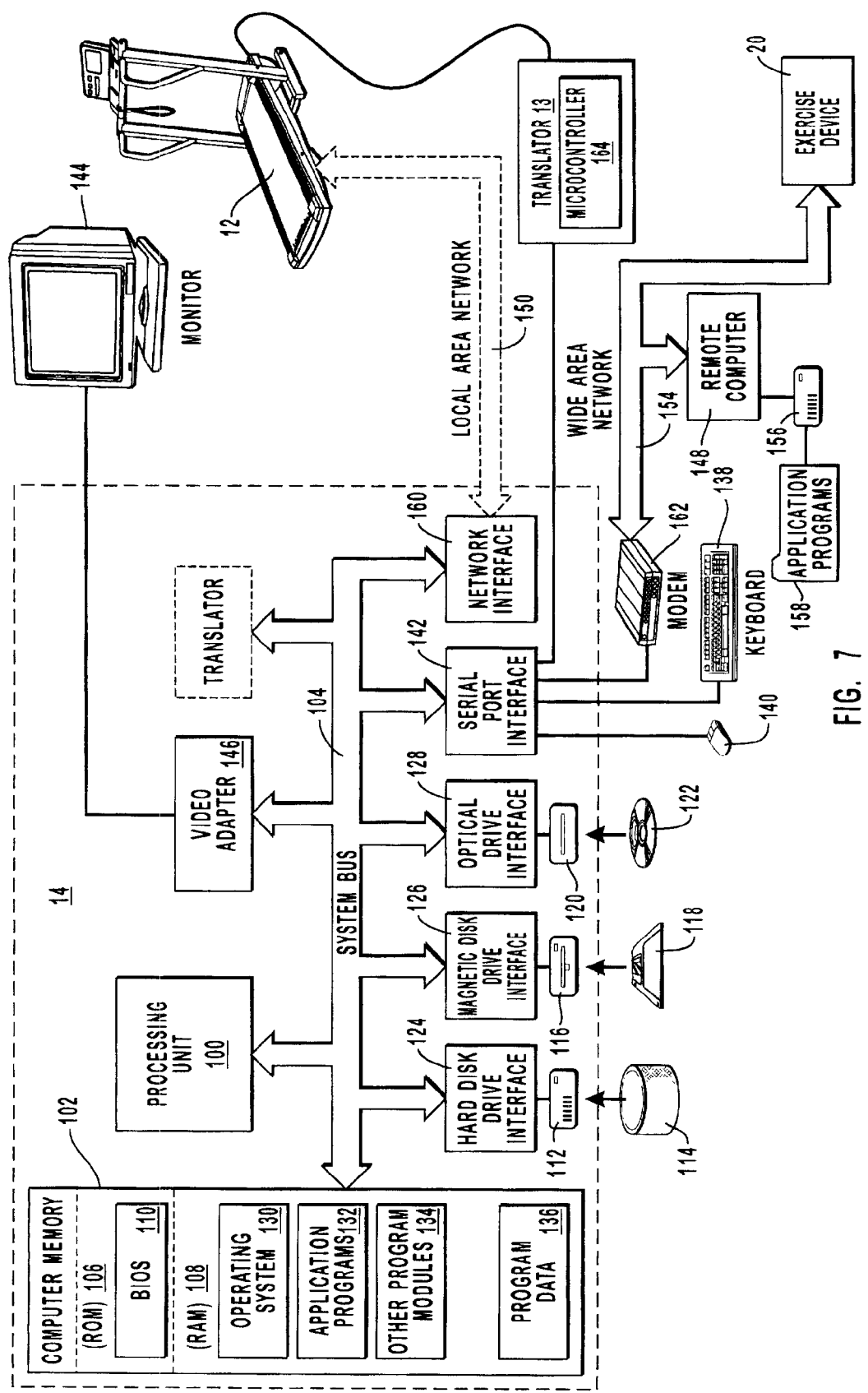
FIG. 7 is an exemplary schematic representation of the computer device and translator device of FIG. 2.

The logical connections depicted in FIG. 7, including LAN 150 and WAN 154, are presented by way of example and not limitation. When used in a LAN networking environment, computer device 14 is typically connected to LAN 150 through a network interface or adapter 160 that communicates via one of a variety of hardwired and/or wireless communication line connections. When used in a WAN networking environment, computer device 14 may include a modem 162, a wireless link (not shown), a T-1 connection (not shown), or other means for establishing communication over WAN 154, such as the Internet. Modem 162, which may be internal or external to computer device 14, is connected to computer bus 104 via serial port interface 142.

As illustrated in FIG. 7, translator device 13 may be connected to computer bus 84 via, for example, serial port interface 142. Translator device 13 may also be connected to treadmill 12 to translate data or signals deliverable by an exercise communication protocol or a computer communication protocol between treadmill 12 and computer device 14, thereby enabling two-way communication. The translation is performed by microcontroller 164, which can be an integrated chip designed for the specific task of translating the data or signals deliverable by an exercise communication protocol to data or signals deliverable by a computer communication protocol, or vice versa. Stated another way, translator device 13 includes interface means for communicatively coupling the exercise device to the computer device and means for generating computer data and/or exercise data that is deliverable, respectively, in accordance with a computer communication protocol and an exercise communication protocol.

Although reference is made to a separate translator device, it can be understood that the structure and/or functionality of translator device 13 may be internal to computer device 14 and/or treadmill 12, but perform the same function of translating data from one protocol format to another to enable an exercise device to bi-directionally communicate with a computer device, whether such computer device is local or remote from the exercise device.

Thus, computer device 14 and translator device 13 are respectively examples of a computer device and translator device that may be employed to exchange information with an exercise device, such as treadmill 12. As provided above, computer device 14 and/or translator device 13 may be internal or external to an exercise device. Further, the exercise device may be configured to format sensed data for delivery directly to the computer device using a computer communication protocol without the need, whether internal or external to the exercise device, for the structure and/or functionality of a translator device.

As will be appreciated by one skilled in the art, the connections provided herein are exemplary and other means for establishing communication between a computer device and an exercise device may be employed in accordance with the present invention.

Two-Way Communication Translation

As mentioned above, embodiments of the present invention relate to communicating information between exercise devices and computer devices. The following discussion will be directed to an exemplary system that includes an exercise device, a computer device, and a translator device separate from the computer device and the exercise device, such as the system illustrated in FIGS. 1 and 2. Although this is one embodiment, as discussed and illustrated herein, alternate systems of the present invention can include the structure and/or functionality of the translator device within the computer or the exercise device or excluded from the computer or exercise device.

Treadmill 12 and computer device 14 of FIG. 1 typically employ different transmission or communication protocols including connection orientated or connectionless networks via asynchronous transfer mode (ATM) technology, X.25 protocol, Frame Relay protocol, packet switching protocols, circuit switching protocols, dynamic packet switching protocols, 802.11RF protocol, home network protocols, CSAFE 1, CAN protocols, and the like. In one embodiment, computer device 14 is configured to receive and transmit data that is formatted in accordance with the RS-232 serial connection or protocol, while treadmill 12 is configured to receive and transmit data that is formatted in accordance with a serial I$^2$C connection or protocol. As such, when treadmill 12 and computer device 14 employ different protocols, communication exchanged between the two devices is prevented. Therefore, translator device 13 is provided between treadmill 12 and computer device 14 to manipulate communication sent in one format into a format that the other device is able to understand.

Translator device 13 includes one or more microcontrollers that convert the communication or signals into a protocol format that the device to receive such signals understands. For example, when computer device 14 communicates via a serial RS-232 connection and treadmill 12 uses a serial I$^2$C connection or protocol, translator device 13 manipulates the serial RS-232 signal received from computer device 14 into a signal capable of being delivered to treadmill 12 via a serial I$^2$C connection or bus. Similarly, translator may manipulate a signal formatted in accordance with the I$^2$C protocol from treadmill 12, into an RS-232 protocol format for computer device 14.

In addition to microcontrollers, translator device 13 includes one or more interfaces that enable signals or data to be received from exercise device 12, computer device 14, communication system 18, and/or third party 21 (FIG. 1). In one embodiment, one interface is a RS-232 jack or port through which data or signals are transmitted or received (hereinafter "transceived") to and from computer device 14, communication system 18, and/or third party 21 (FIG. 1). Further, another interface is an I$^2$C port through which data or signals are transceived to and from exercise device 12.

The interfaces 184, 178 are each structures capable of performing the function of interface means for communicatively coupling the exercise device to a computer device and/or communicatively coupling the computer device to the exercise device. Further, communication interface 90 is another structure capable of performing the function of interface means for communicatively coupling the exercise device to a computer device and/or communicatively coupling the computer device to the exercise device.

Although reference is made to specific ports or interfaces, one skilled in the art can identify various other interfaces or interface means, such as but not limited to, a modem interface, a cable modem interface, an ADSL interface, an ISDN interface, an Ethernet interface, a wireless interface, an IR interface, a fiber-optic interface, an electromagnetic radiation interface, or the like. Further, the interfaces or interface means can be adapted to accommodate microwave technology, satellite, blue tooth transmission, home network protocols, or various other protocols and technology as known by one skilled in the art.

Generally, as will be appreciated by one skilled in the art, each connection interface or interface means of translator device 13 communicates with a microcontroller of translator device 13 and with an exercise or computer device interface, as will be further demonstrated below.

The translator device is one example of structure capable of performing the function of means for generating computer data and/or exercise data. It can be appreciated by one skilled in the art that various other configurations of translator device and means for generating are known to those skilled in the art. For example, processor 88, alone or in combination with processor 92, is another structure capable of performing the function of means for generating, where the exercise data is any measurable parameter of the exercise device and/or the user of the exercise device identified by the exercise device.

The communication or signals passed through translator device 13 may include data, audio, video, and/or control signals. As such, the connection interfaces of translator device 13 may be of a variety of types depending on the particular transmission medium and/or protocol used at each interface, including a wireless interface that uses infrared (IR) or radio frequency (RF).

Figure 8:
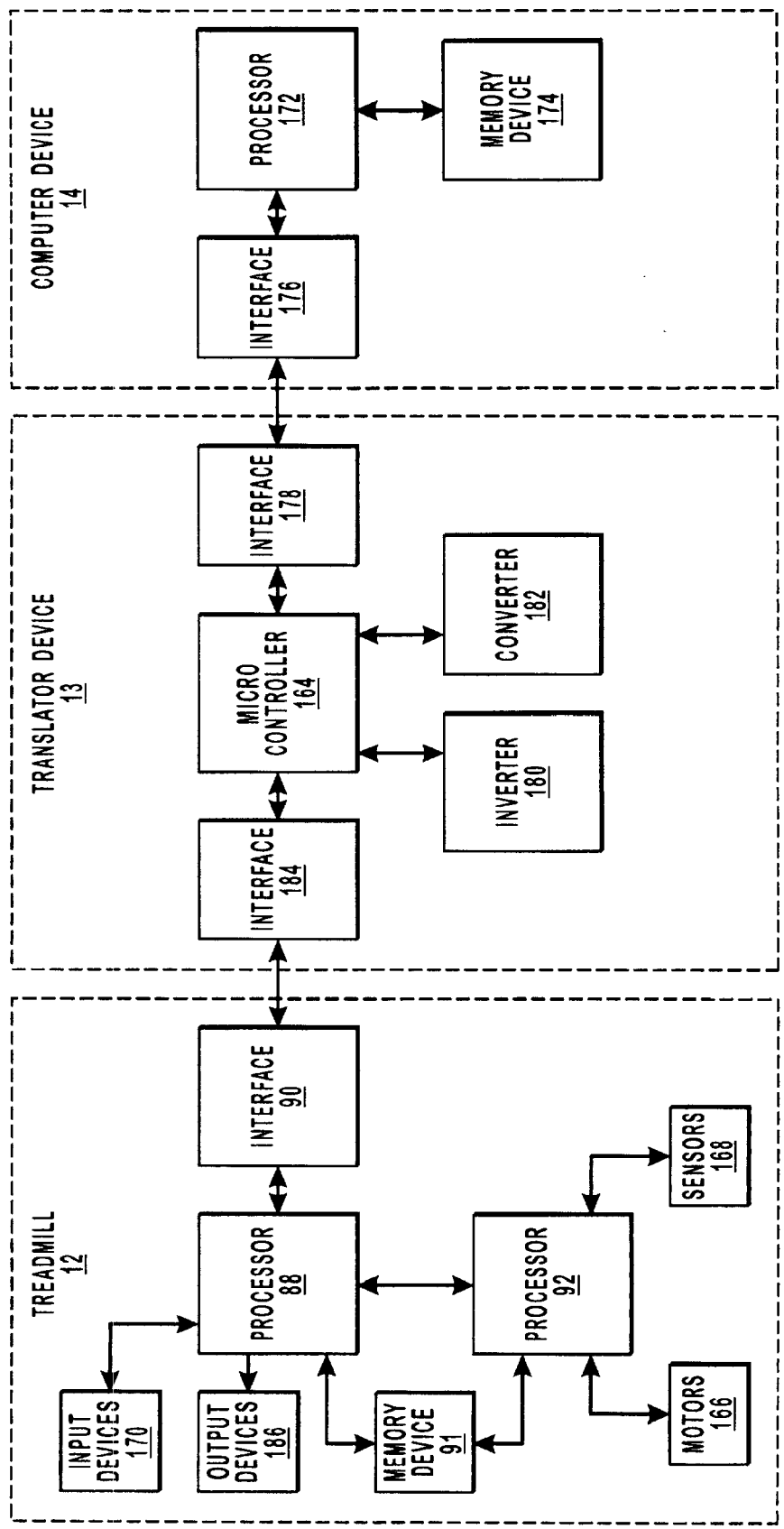
FIG. 8 is a block diagram representation of two-way communication enabled in the exemplary system of FIG. 2.

With reference to FIG. 8, a block diagram is provided that includes treadmill 12, computer device 14 and translator device 13. Treadmill 12 is configured to allow a user to exercise thereat and to gather device data and/or user data that may optionally be preserved in internal memory. Examples of device data include information relating to the exercise device, including speed, resistance, incline, time, temperature, and other similar operating parameters. The device data may be gathered by a processor, such as processor 92, from various motors 166, sensors 168 and/or controllers (not shown), and preserved in memory device 91. Examples of user data include information relating to the user of the exercise device, such as the user's age, weight, height, current pulse rate, and other information specific to the user. A processor, such as processor 88 or 92, gathers user data from sensors 168 or input devices 170 and preserves the user data.

A. Communication Initiated by a Computer Device

At times, it is advantageous for a computer device to access the exercise device and/or user data preserved at an exercise device. For example, computer device 14, communication system 18, third party 21, and/or other computer devices, translator devices, or exercise devices may track the performance of the user and monitor the current pulse rate of the user exercising on treadmill 12 to provide an aerobic workout without forcing the pulse rate to a hazardous level. Alternatively, computer device 14, communication system 18, third party 21, and/or other computer devices, translator devices, or exercise devices may access the exercise device to modify, reconfigure, or set up parameters or software internal to treadmill 12 and/or to perform a diagnostic check on treadmill 12. The functionality and/or structure of the translator device enable communication between computer device 14, communication system 18, third party 21, and/or other computer devices, translator devices and treadmill 12. Alternatively, the exercise device can transmit data to and receive data from computer device 14 without the aid of the translator device, such as when processor 88 is capable of receiving data indicative or any measurable parameter of the exercise device and/or the user of the exercise device and formatting the same for delivery to the computer device using a computer communication protocol.

The following discussion will make reference to receipt and delivery of data between treadmill 12 and computer device 14 through translator device 13. It can be appreciated, however, that similar discussions can be made for communication between treadmill 12 and communication system 18, third party 21, other computers, or exercise devices directly, without a translator device, or through a translator device, whether such translator device is a separate hardware and/or software component or incorporated within treadmill 12, communication system 18, third party 21, other computer devices, or exercise devices.

In one embodiment, RS-232 is the computer communication protocol used by computer device 14 to request data from memory 91, 93, 95 or processor 88 of exercise device 12. The RS-232 protocol allows for the user of structured commands to selectively read any byte of memory 91, 93, 95 or processor 88, such as a byte of RAM, thereby providing computer device 14 with unlimited accessibility to data at treadmill 12. For example, RS-232 commands may be used by computer device 14 to obtain device data and/or control operating parameters of treadmill 12, such as the desired speed, current speed, incline status, measurement type employed, time, distance, total time, total distance, total calories, console identification, actual time, actual distance, actual calories, service time, serial number, part number, and the like from treadmill 12. Furthermore, computer device 14 may utilize RS-232 commands to obtain user data such as a user's weight, amount of calories burned, current pulse rate, age, gender, and the like from treadmill 12.

In one embodiment, a packet structure is used to communicate information between computer device 14 and treadmill 12. For example, a structure for sending a cluster of information may include a command or identifier byte followed by a length byte that gives the length of the packet beyond the length byte. Thus, if the length byte=0 in a packet of information, the packet would only include the command byte and the length byte. In the event that there were three additional bytes beyond the length byte, then the length byte would equal three and the total packet size would be five. The packets of data are optionally compressed and encapsulated for transmission between computer device 14 and treadmill 12. Although reference is made to specific packet sizes and byte lengths, one skilled in the art can identify various other packet structures that are capable of performing the desired function.

With reference to FIG. 8, in one illustrative embodiment, when it is desirous for computer device 14 to access data from memory device 91, or other memory or processor of exercise device 12, and/or control operating parameters of exercise device 12, an RS-232 protocol request is generated by processor 172 and sent to translator device 13, using interface 176. Translator device 13 receives the RS-232 protocol request at interface 178, which is an example of means for communicatively coupling the computer device to the translator device and/or the exercise device, means for receiving computer data from the computer device, and means for delivering computer data to the computer device. It can be understood by one skilled in the art that such means can also include one or more of microcontroller 164, an inverter 180, a converter 182, and interface 184.

The request received at interface 178 is translated into an I²C protocol request by microcontroller 164, which is an example of means for generating exercise data deliverable to the exercise device and means for generating computer data deliverable to the computer device. Other means are known to one skilled in the art. For instance, such means can include one or more of inverter 180 and converter 182.

Inverter 180 inverts digital signals as necessary to provide isolation protection against static and other noise, and to assert signals in a proper state when it is necessary that the signal be sent in an opposite state. Converter 182 provides a modification to voltage ranges to facilitate translation of the signals from one format to another. For example, a voltage range at the serial port at computer device 14 may range from about +15 volts to about −15 volts or from about −10 volts to about +10 volts, while the voltage range at the microcontroller 164 may range from about +5 volts to about 0 volts. Although reference is made to specific voltage ranges, one skilled in the art can appreciate that various other ranges are appropriate.

Generally, inverter 180 and converter 182 facilitate buffering of the signals transceived, i.e., received and/or transmitted, between the exercise device and the computer device. Therefore, one skilled in the art can identify various other software and/or hardware modules that are capable of acting or functioning as a buffer for the signals transceived between the computer device and the exercise device.

Once microcontroller 164 translates the RS-232 serial protocol request into an I²C protocol request, the I²C protocol request is sent to treadmill 12 by interface 184, which is another example of interface means for communicatively coupling the computer device to the translator device and/or the exercise device, means for receiving exercise data from the exercise device, and means for delivering exercise data to the exercise device. It can be understood by one skilled in the art that such means can also include one or more of microcontroller 164, an inverter 180, a converter 182, and interface 184.

Treadmill 12 receives the I²C protocol request at interface 90 and a processor, such as processor 88 and/or 92, generates a response to the request by accessing the corresponding data from memory device 91 and sending an I²C response to translator device 13 via interface 90. Translator device 13 receives the I²C response at interface 184 and translates the I²C response into an RS-232 protocol response at microcontroller 164. The RS-232 protocol response is then sent from translator device 13 to computer device 14 via interface 178. Computer device 14 receives the RS-232 protocol response at interface 176. As such, using a translator device, a computer device may obtain data from an exercise device.

As can be understood by one skilled in the art, in light of the teaching contained herein, other manners of facilitating communication between the exercise device and the computer device are known. For example, one or more of microcontroller 164, inverter 180, and/or converter 182 can be included within treadmill 12 and/or computer 14. In another configuration, microcontroller 164, inverter 180, and/or converter 182 can be included within processor 88 of treadmill 12, with interface 90 performing the function of interface 178 and/or interface 184. Similarly, microcontroller 164, inverter 180, and/or converter 182 can be included within processor 172, with interface 196 performing the function of interface 184 and/or interface 178. In another configuration, treadmill 12 communicates directly with computer device 14 when processor 88 is capable of converting data indicative of any measurable parameter of treadmill 12 and a user exercising using treadmill 12 and formatting the data for delivery using the computer communication protocol through interface 90, such as in the form of a RS-232 port, or the like.

Figure 9:
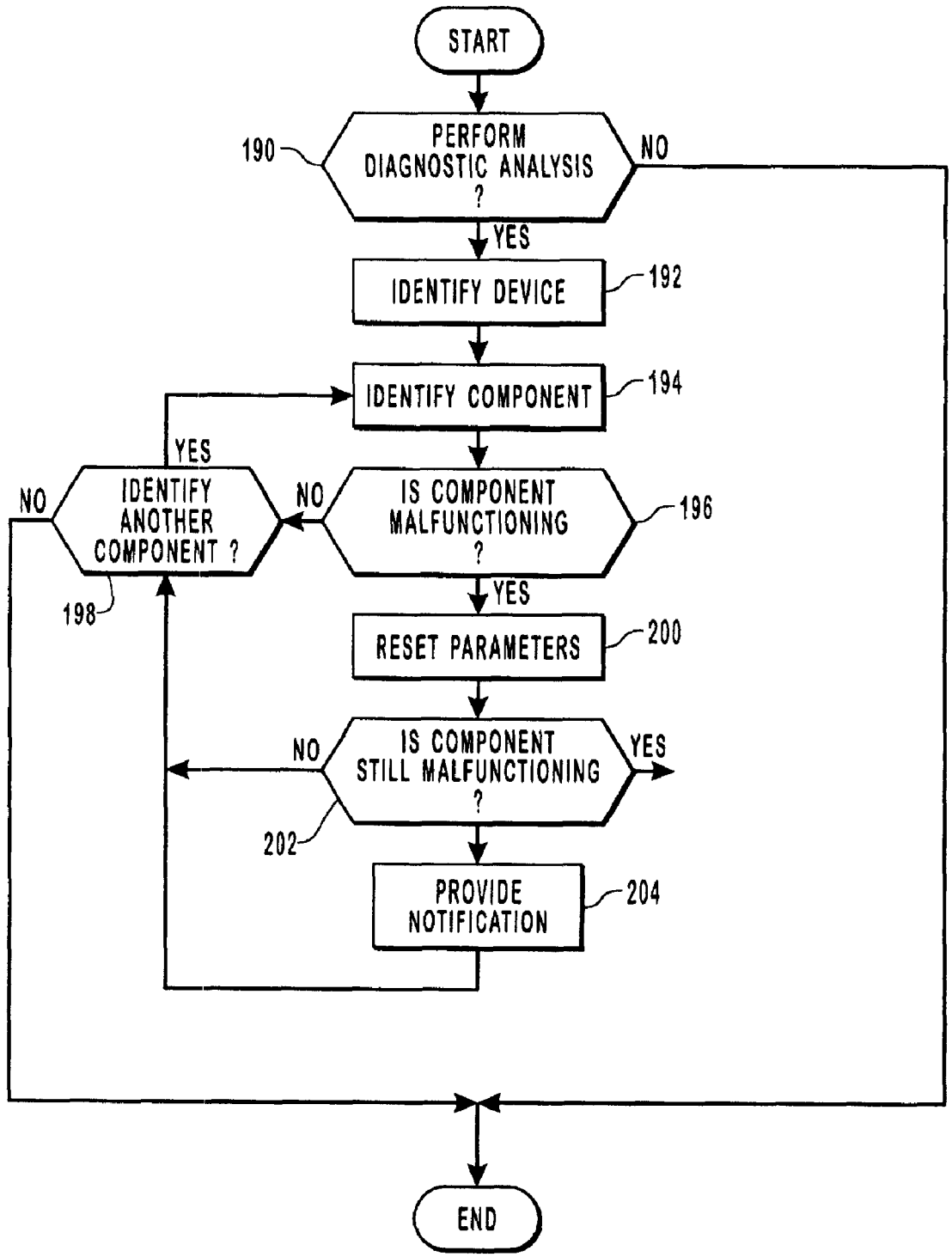
FIG. 9 is a flow chart that provides an example of an exchange that may be made between a computer device and an exercise device enabled by the translator device.

With reference to FIG. 9, a flowchart is illustrated that provides an example of communication initiated by a computer device that is enabled by the use of a translator device located between an exercise and computer devices. In the example, the communication is in the form of an automatic diagnostic check or analysis performed on treadmill 12 by computer device 14. A diagnostic analysis enables, for example, computer device 14 to monitor treadmill 12 and automatically program or reset parameters.

The flow chart of FIG. 9 is one example of communication initiated by a computer device that is enabled using a translator device. As illustrated, the computer can determine whether to perform a diagnostic process on the exercise device, as represented by block 190. For instance, the computer device can store a list of exercise devices that typically connect to the computer device and data indicative of when these exercise devices were last checked for problems, availability of new software, or the like. When an exercise device connects to the computer device, the computer device checks the newly connected exercise device against the stored list and determines whether to initiate a diagnostic process. Alternatively, the computer device can initiate a diagnostic process each time an exercise device connects to the computer device or when new software updates or the like are available for the exercise device.

Once the computer device determines that a diagnostic process is to commence, the computer device identifies the exercise device and current data or information about the exercise device, as represented by block 192. Illustratively, the computer device can access stored information about the exercise device, the problems that have occurred in the past, what changes have previously been made to the hardware and/or software associated with the exercise device, or the like. Upon identifying the exercise device, the computer device selects a first component or module, as represented by block 194. This selection can be based upon prior problems with the exercise device, availability of software updates, a stored list of those components to check and in a particular order, combinations thereof, or the like.

In the event that the component is not malfunctioning, as represented by decision block 196 being in the negative, the computer device determines whether other components are to be checked, as represented by decision block 198, and either identifies a subsequent component or terminates the diagnostic process.

In the event that the component is malfunctioning, as represented by decision block 196 being in the affirmative, the computer device resets the operating parameters related to the component, as represented by block 200. Alternatively, the computer device can update the software, reprogram the microprocessor, combinations thereof, or the like.

Once the software has been reset, update, reprogrammed, or the like, the computer device tests the component to determine the status of the component, i.e., is the component still malfunctioning, as represented by decision block 202. When the component is functioning correctly, as represented by decision block 202 in the negative, the computer device determines whether other components are to be checked, as represented by decision block 198, and either identifies a subsequent component or terminates the diagnostic process.

Alternatively, in the event that the component continues to malfunction, as represented by decision block 202 in the affirmative, the computer device delivers a notification to the provider or owner of the exercise device that details the problem and indicates the need to request additional assistance at the location of the exercise device to repair the problem, as represented by block 204. The notification can be an electronic mail message (email) to the provider of the exercise device, such as when the exercise device is in a gym, club, or the like or to the owner of the exercise device. Alternatively, the notification can be a message displayed on the video output device of the exercise device, the illumination of a light on the control panel indicating an error or problem with the exercise device, or some other manner known to one skilled in the art. In still another embodiment, the notification can include notifying a service center that subsequently contacts the owner or operator the exercise device, such as by telephoning, emailing, postage mailer, or the like.

Upon providing the notice of a problem or error with the component and/or the exercise device, the computer device determines whether other components are to be checked, as represented by decision block 198, and either identifies a subsequent component or terminates the diagnostic process.

In addition to performing a diagnostic process on an exercise device, the translator device enables the computer automatically or in response to instructions from some other computer device or individual to: (i) set-up internal parameters of the exercise device upon identifying specific components included in the exercise device; (ii) monitor the current status of a user, such as the user's current pulse rate, to maintain an appropriate workout and/or to prevent the user from entering into an unhealthy or hazardous region or level; (iii) monitor and optionally provide an amount of resistance experienced by the user of the exercise device, such as regulating the amount of resistance provided by an electronically controlled weight stack of a weight lifting device; (iv) deliver new versions of software used by the exercise device and cause such software to be installed on the exercise device; (v) reconfigure internal components of the exercised device, such as the microprocessor, audio/video controller, treadmill controller, or the like; and (vi) perform other computer initiated communications.

B. Communication Initiated by an Exercise Device or User

Communication between an exercise device and a computer device that is enabled by a translator may further allow for information located at a computer system or device to be accessed by an exercise device or user at the exercise device. For example, with reference back to FIG. 8, computer device 14 may include a recorded exercise program preserved in memory device 174. Therefore, treadmill 12 may provide an I²C request to obtain the exercise program from memory device 174. The I²C request is sent to interface 184 of translator device 13, which translates the I²C request into an RS-232 protocol request by microcontroller 164 and uses interface 178 to forward the RS-232 request to computer device 14.

Processor 172, upon receipt of the RS-232 protocol request, obtains the exercise program from memory device 174 and transmits it to translator device 13, which translates the transmission from an RS-232 protocol to an I²C protocol and sends the I²C protocol transmission to treadmill 12. The exercise program is then provided to the user on output devices 186 and/or used to control motors 166. The exercise program provided by computer device 14 may be a stored program. In another embodiment, the exercise program may be provided by a live trainer. Furthermore, the exercise program may be provided in real time or on a delayed basis.

Other data that may be provided by computer device 14 to treadmill 12 includes entertainment information, such as an audio program and/or video program, motivational content, electronic books or magazines, health information, purchase information, or other information that may be provided to the user while the user exercises at treadmill 12, such as discussed in co-pending U.S. patent application Ser. Nos. 09/641,600, 09/641,220, 09/641,627, 09/349,608, and 09/496,560.

Thus, in accordance with the systems and methods of the present invention, bi-directional communication is enabled in a fitness environment that includes at least one exercise device and at least one computer device. The communication is enabled by a translator that includes a microcontroller for translating protocol formats to enable two-way communication between the computer device and the exercise device.

In addition to enabling different computer devices and exercise devices to communicate one with another, embodiments of the present invention enable a user to compete as part of a virtual race through use of the user's exercise device. Consequently, embodiments of the present invention relate to enabling one or more users on one or more exercise devices to interact in a competitive environment, regardless of network latency and when the users participate in such interaction.

User Competition

Communication between an exercise device and a computer device utilizing the systems and methods of the present invention enable a user to participate in a competitive environment while exercising on the exercise device. The competitive environment within which the user can participate "virtually" includes racing against previous races of that user that are stored at the treadmill, the computer device, and/or the communication system. Further, the competitive environment includes (i) competitive races with preprogrammed or stored exercisers, races, times, or courses; (ii) competitive races against one or more users exercising in real-time; (iii) competitive races against one or more user exercising in a delayed time basis; and/or (iv) combinations thereof, or the like. The competitive environment is advantageous to a user in that it provides motivation to the user while he/she is exercising.

The races are termed "virtual races" because the user is exercising on a computer-generated course, optionally racing against imaginary or virtual users, optionally racing against stored races of that user, other live users, or time-delayed live users. Therefore, the term "virtual race" includes: (i) racing on a computer generated virtual course, whether such virtual course is mapped from actual terrain or created from virtual terrain; (ii) racing against a stored race performed by the user; (iii) racing against imaginary exercisers; (iv) racing against live users, but in a time-delayed setting; (v) racing against a live user that is exercising upon another exercise device; (vii) or the like. The interaction between exercise devices and users can be achieved through use of the systems, methods, devices, modules, and components of the present invention, combinations thereof, or the like.

The data representative of each course associated with each virtual race includes control signals deliverable to the exercise device, computer device, and/or translator device. These control signals can vary one or more operating parameters of the exercise device as the user follows the course. For instance, when the user reaches an incline or decline in the course associated with the virtual race, the control signals received by the exercise device will cause the exercise device, such as a treadmill, to vary the inclination or declination of the tread base in accordance with the virtual inclination or declination of the course.

Figure 10:
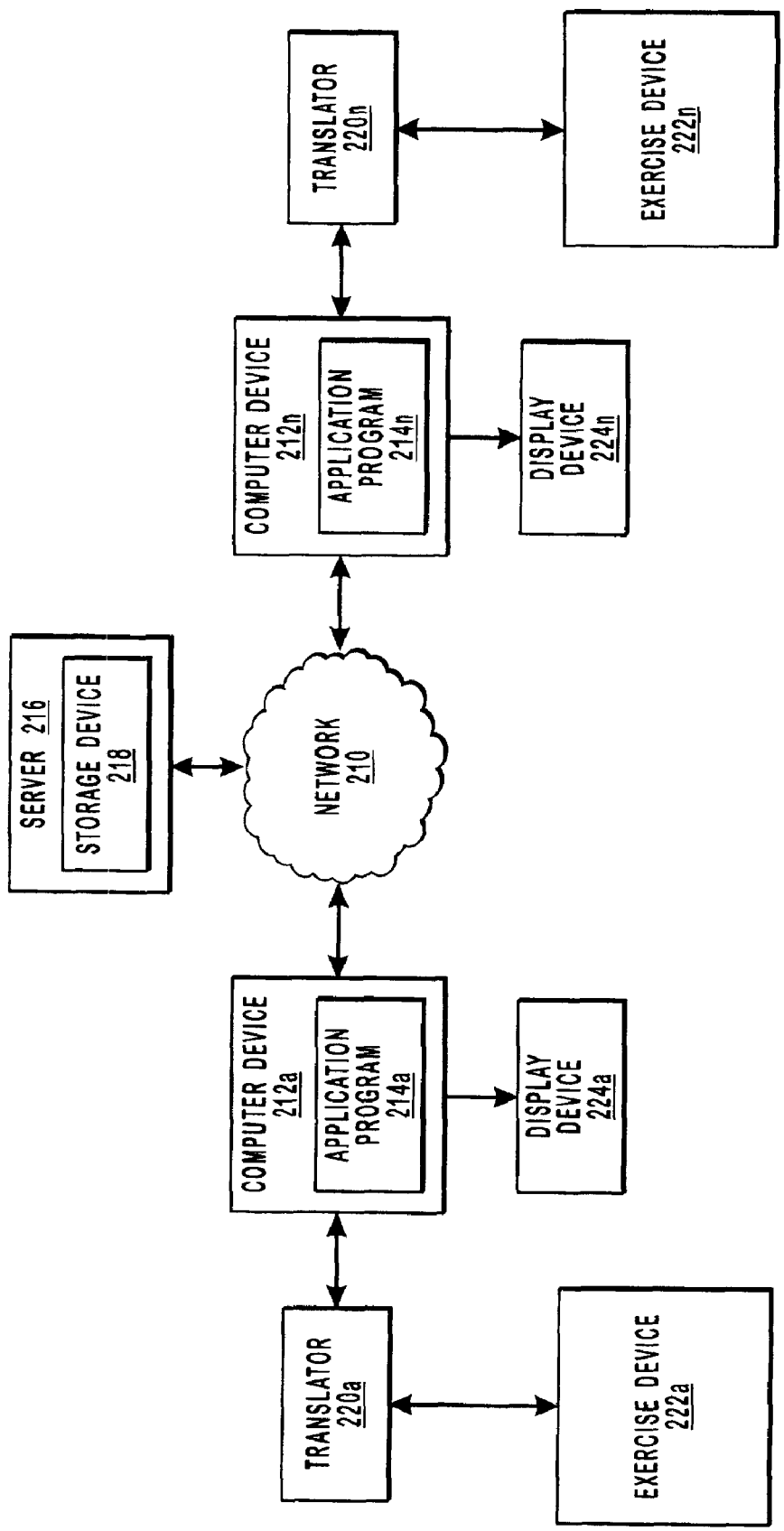
FIG. 10 is a block diagram representation of an exemplary system configuration to enable competitive user interaction on home fitness equipment.

With reference to FIG. 10, a block diagram representation of an exemplary system configuration is illustrated that enables competitive user interaction on one or more exercise devices, i.e., enables one or more users to compete in a virtual race. Although reference is made to a particular system 200, one skilled in the art can appreciate that various other systems are applicable for use with the present invention. For instance, other systems can includes those described in co-pending U.S. patent application Ser. Nos. 09/641,600, 09/641,220, 09/641,627, 09/349,608, and 09/496,560.

In FIG. 10, a network is illustrated as network 210, which may be similar to network 16 (FIG. 1), such as a Local Area Network ("LAN") or a Wide Area Network ("WAN"), such as the Internet. Connected to network 210 are one or more computer devices, illustrated as computer devices 212a–212n and server 216, which includes storage device 218. Each of the computer devices 212a–212n are in turn connected to a translator device 220a–220n, which is in turn connected to an exercise device 222a–222n, as provided in the discussion above. Computer devices 212a–212n are also connected to an output device, illustrated as display device 214a–214n, which may be used to enhance competition. The devices and programs of the presently described embodiment of the present invention can utilize the functionality and structures of those devices and programs described previously herein. For instance, computer devices 212a–212n, translator devices 220a–220n, and exercise devices 222a–222n can be similar or dissimilar from computer devices 14, translator devices 13, and/or exercise devices 12. Further, server 216 can have similar or dissimilar structures and functions to communication system 18 described herein and in co-pending U.S. patent application Ser. Nos. 09/641,600, 09/641,220, and 09/641,627.

In accordance with one embodiment of the present invention, a first user on a first exercise device, such as exercise device 222a, at a first location may compete against a second user on a second exercise device, such as exercise device 222n, at a second location, even when the locations are in separate cities, states or even countries. Each of the exercise devices 222a–222n communicates through translator devices 220a–220n to computer devices 212a–212n. An application program 214a–214n resides on computer devices 212a–212n. The application programs 214a–214n provide, for example, images and other information to enable a competitive race between one or more users. The use of the application programs 214a–214n lessens the requirements for bandwidth between server 216 and computer device 212a–212n, translator device 220a–220n, and/or exercise device 222a–222n.

The obtaining of application programs 214a–214n may be performed in a variety of manners as understood by one of ordinary skill in the art, including loading the application programs 214a–214n onto computer devices 212a–212n through the use of a floppy diskette or a compact disk, by receiving application programs 214a–214n from server 216 when network 210 is a LAN or WAN, such as the Internet.

In one embodiment, the first and second users independently access server 216 through computer devices 212a and 212n to schedule a race or competition. Just before a start time, the first and second users begin exercising on their exercise devices, respectively exercise devices 222a and 222n. The race begins, in one embodiment, while the users are exercising and the corresponding computer devices 212a and 212n control the layout of the race using application programs 214a and 214n, respectively. Throughout the race, each computer device 212a and 212n and/or exercise device 222a and 222n monitors, with respect to the start time of the race for a user, the distance traveled by that user while he/she is exercising. For instance, each exercise device 222a–222n and/or computer device 212a–212n can track the revolutions per minute of the exercise device belt, such as when exercise device 222a–222n is a treadmill, to identify the distance traveled by the user. When the exercise device is an exercise cycle, exercise device 222a–222n and/or computer device 212a–212n can track the revolutions per minute of the exercise cycle wheel or crank.

One skilled in the art can identify various other manners to track the distance traveled by the user and the time in which such distance is traveled. For example, the exercise devices 222a–222n are treadmills, the race layout is controlled by the computer devices 212a–212n regulating the incline of the tread base of each treadmill to correspond to the preprogrammed terrain of the race. The terrain may simulate a variety of courses, including a racetrack, a cross-country course, a mountainous course, a residential course, etc. Each user is able to independently set and/or modify the belt speed of the treadmill to regulate the user's speed during the race.

As computer devices 212a and 212n and/or exercise devices 222a–222n monitor or track the user performance at exercise devices 222a and 222n to determine the distance traveled by each user, the current position of each user in the race is communicated from computer devices 212a, 212n to server 216 across network 210. Server 216 then compares the user performance information from computer devices 212a, 212n and/or exercise device 222a–222n. Alternatively, the comparing of user performances may be performed at one of the computer devices 212a, 212n. In still another configuration, the comparing of user performances can be performed at the respective treadmill, translator device, or computer device and data indicative of the comparison delivered the other treadmills, translator devices, computer devices, or servers of the system.

Once the user performances have been compared, server 216 communicates all of the various race positions to each of the clients, illustrated as computer devices 212a, 212n, and/or exercise devices 222a, 222n, to allow for a display of the relative user positions in the race on display devices 224a, 224n and/or display devices of exercise devices 222a, 222n, such as those display devices discussed with respect to exercise device 12.

Once the race ends, each computer device 212a, 212n obtains race results for the user at the corresponding exercise device and uploads the user competition information to server 216 via network 210, which is an example of a means for providing communication between a first client, a second client, and a means for comparing. Alternatively, such as when the exercise devices are monitoring and tracking the performance of the user exercising thereat, the exercise device can upload the user competition information to server 216, without using a separate computer device.

At server 216, the competition information for all users is processed or compared while the users are experiencing a cool down routine at exercise devices 222a, 222n. Once processed, a winner of the virtual race is determined by server 216 and is communicated to each computer device 212a, 212n across network 210. The official results of the virtual race are then provided for the participants on display devices 224a, 224n, respectively. Alternatively, server 216 can deliver the official results to exercise devices 222a–222n, which present the results to the user(s) through user of one or more output devices, such as those described herein and others know to one skilled in the art in light of the teaching contained herein.

While the example above refers to two users racing against each other at the same time, embodiments of the present invention embrace a variety of scenarios. For example, a single user may race against previously races performed by the user and stored at the exercise device, the computer device, the communication system, or the like. Further, a single user may race against prerecorded competitors or a large number of users may compete over the network. Alternatively, the competitors may race at different times, such as when a first user competes in the morning of a first day and a second user competes in the evening of a second day. When the users race at different times the first user to compete may run the race and then return after all other competitors have run the race to be informed of the official results of the race. Thus, once all of the users have completed the race, the server processes the data and each of the participants are notified of the winner and optionally the order in which the participants finished the virtual race.

The users are able to participate in a competitive environment while exercising, regardless of when the race was run by the various competitors. Moreover, since the computer devices and/or the exercise devices track user performance and the results are processed at the server and communicated to all participating computer devices and/or exercise devices, individually "clients", users are also able to participate in a competitive environment while exercising regardless of network latency. For instance, the exercise data is generated at the exercise device and uploaded to the server or means for comparing as the users compete. A delay in the server comparing the received data and delivering data indicative of the position of each competing user does not affect the exercising activities of the users. Through identifying the winner and order in which the users completed the race during a cool down time, a delay in the display of the race winner and order by which the other users completed the race does not affect the motivational affect upon the users as the compete in a virtual race.

Figure 11:
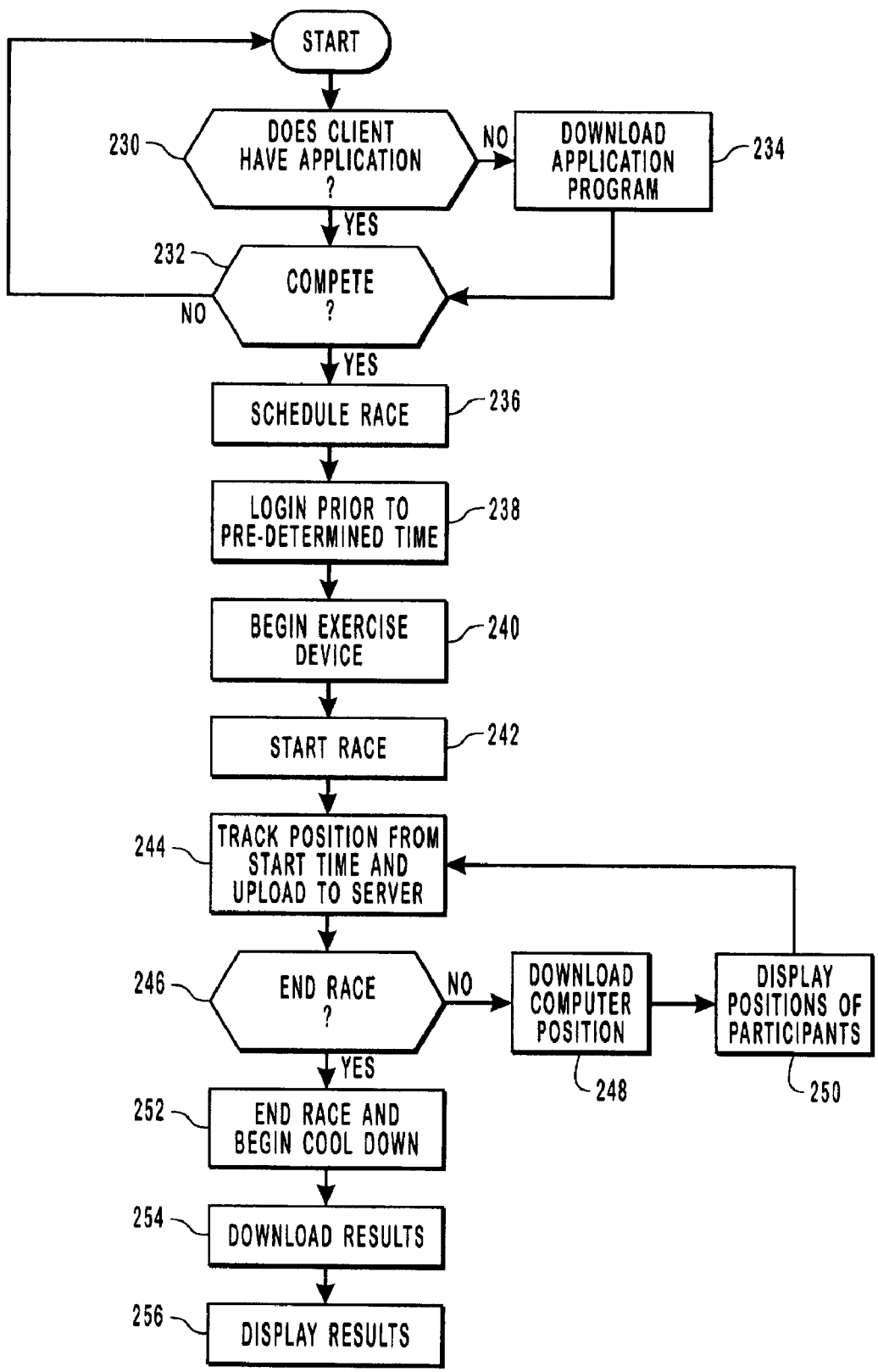
FIG. 11 is a flow chart that provides an example of the processing performed at each client computer of FIG. 10 to enable the competitive user interaction.

With reference to FIG. 11, a flow chart is provided that illustrates an example of the processing that may be performed at each computer device illustrated in FIG. 10 to enable the competitive user interaction. Although reference is made to the processing performed at each computer device, it can be appreciated by one skilled in the art that when the functionality of the computer device is incorporated within each exercise device, each exercise devices can performed the processing described herein and such other processing as known by one skilled in the art in light of the teaching contained herein.

In FIG. 11, when the computer device connects to the server it is determined whether the computer device has access to or installed thereupon the application program, as represented by decision block 230. This can be achieved by the server accessing a list or table stored on the computer device of installed or accessible applications.

Alternatively, the server can maintain the stored list or table of installed or accessible applications on a per computer or exercise device basis. Upon the computer device or the exercise device that includes the functionality of the computer device accessing the server, the server compares an identifier of the computer or exercise device, such as the device's Internet Protocol address, against the stored list or table to determine whether the appropriate application program is installed or accessible by the computer device.

When it is determined that the application program is not available at the computer device, i.e., decision block 230 is in the negative, the computer device retrieves from the server and/or the server delivers to the computer device the application program, as represented by block 234. For example, when network 210 of FIG. 10 is a WAN, such as the Internet, the application program may be downloaded to the computer device and automatically installed thereupon, as known by one skilled in the art.

Alternatively, in the event that it is determined that the computer device has access to the application program, the computer device next determines whether or not a user desires to participate in a competition, as represented by decision block 232. When decision block 232 is in the affirmative, i.e., a user wishes to participate in a competition, the user can schedule a race, as represented by block 236.

The scheduling of a race can include accessing the server through the computer device, translator, and/or exercise device. The server can take the form of the communication module or system, such as the web site described in U.S. patent application Ser. Nos. 09/641,600, 09/641,220, and 09/641,627.

Upon accessing the server, the user can schedule a time for when the race will be run and a virtual course upon which the race will be run. Further, the user can select which other users they will race against, whether or not such users are virtual exercisers or other exercisers upon other exercise devices. For example, one user exercising on a treadmill can race against another user exercising upon a rowing machine, exercise bike or the like.

Optionally, when the user schedules the competition, the server can generate a race appropriate for each competitor and the exercise device upon which the user is exercising. Illustratively, the server can generate a race where the user exercising on the treadmill will run 5 miles, while the user on the exercise bicycle will travel 20 miles. Consequently, both exercisers traverse the same "relative" distance for the exercise device. This can be achieved by the server accessing the device storage and retrieving course data appropriate for an average exercising user, with the selected difficultly level, for a particular exercising device. For instance, the course for a user exercising upon a treadmill may require 5 laps of a course, while the user exercising upon the exercise bicycle may need to traverse 20 or more laps. In another configuration, the server can retrieve one course for the user exercising upon a treadmill, while another course of equal "relative" length and difficulty can be selected for a user exercising upon a stationary bicycle.

Various other manners are known to one skilled in the art to generate a race that provides substantially equal course based upon the particular type of exercise device being used by the exercising user. Further, embodiments of the present invention enable users to compete using different parameters as the gauge for which user is the winner. For instance, the users can compete based upon the number of calories burned, rather than a distance traversed. Similarly, users can compete based upon performance upon different exercise devices over a course, such that each user is to run a defined distance, row a certain distance, and cycle a certain distance, with the user that traverses the total distance in the shortest time being the winner of the race.

Before the scheduled time for the race, each user of the competition logs into the system, as represented by block 238, and begins exercising on an exercise device, as represented by block 240. The user can login to the server or the applications hosted thereby through entering a credential, such as a username and password, that is authenticated by the server and/or the software hosted thereupon.

While the users are exercising on the exercise devices, such as warming up for the race, the server delivers a notification that the race is about the commence and subsequently begins the race at the defined time, as represented by block 242. The notification can be an audible notification, a visual notification, a tactile notification, combinations thereof, or the like.

As each user exercises, the computer device tracks the distance traveled since the start time of the race to determine the user's current position in the race and uploads the current position of the user to a server on the network, as represented by block 244. The server determines whether the race is completed, as represented by decision block 246. For instance, has the exercise period terminated, has a user completed the race, or the like.

In the event that it is not time to end the race, the server downloads each competitor position in the race to the computer devices, as represented by block 248. Consequently, the computer device delivers the data indicative of the competitor's positions to the translator, which subsequently delivers the data to the exercise device for a display to the participants of the race, as represented by block 250. Optionally, the display device associated with the computer device can display the relative positions of all users in the virtual race.

The computer device and/or the exercise device continues to go through this process of tracking the position of the user, determining whether the race is to end, downloading the position of all other users, and displaying the positions of all competitors until the race is to end, as represented by decision block 246 being in the affirmative.

Once it is determined at decision block 246 that the race is to end, the final time of each user and any other relevant user information is uploaded to the server, and the user begins a cool down period or otherwise waits for the official results of the race, as represented by block 252. The server analyzes the distances and times received from teach user and identifies the finishing order for each participant in the race. Once the official results are calculated, the computer device receives the same from the server, as represented by block 254 and displays the results to each participant, as represented by block 256. The display of the results may include, for example, who won the race and what the ending positions of each of the participants were of the virtual race.

Figure 12:
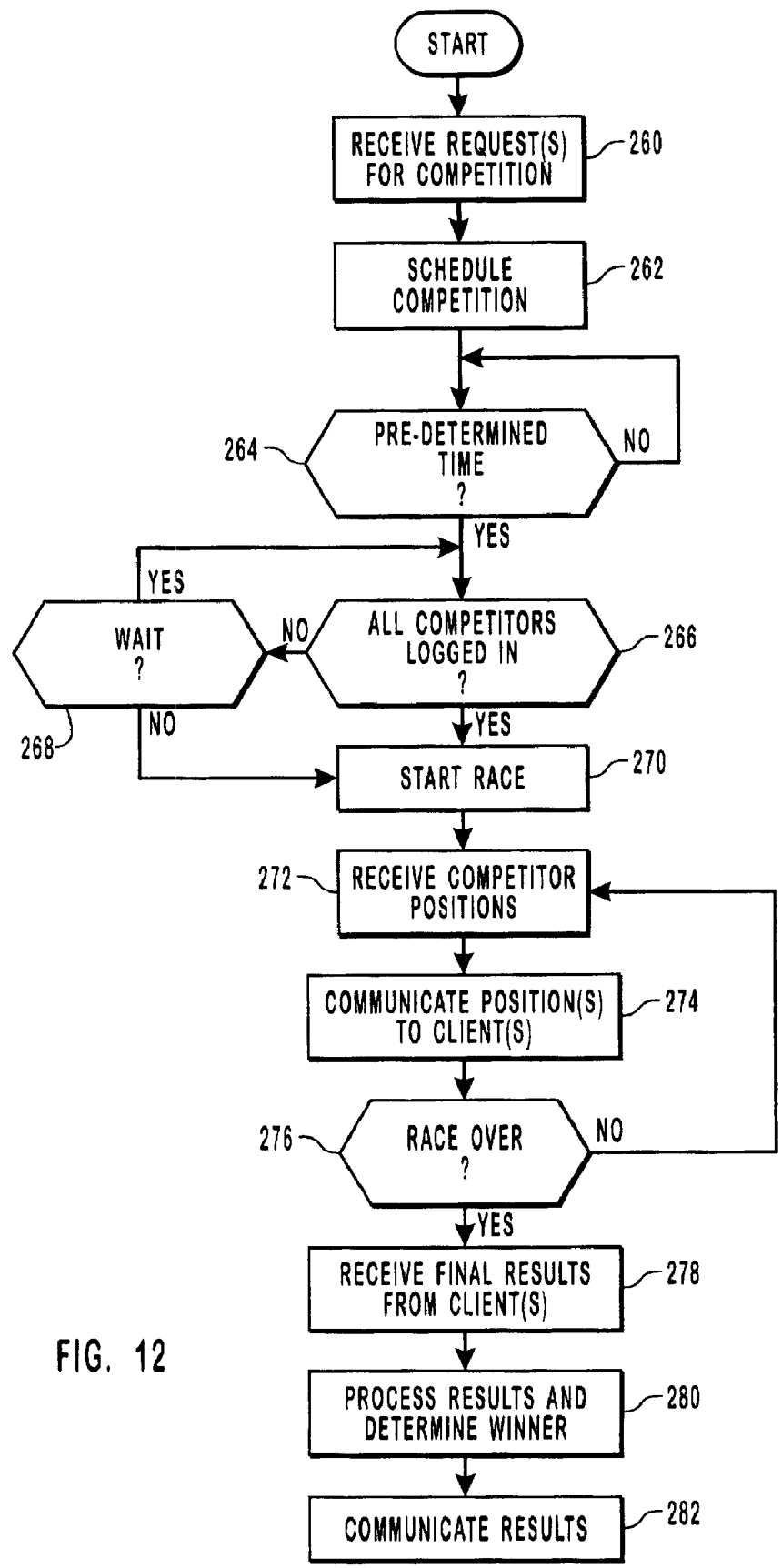
FIG. 12 is a flow chart that provides an example of the processing performed at the server of FIG. 10 to enable the competitive user interaction.

With reference to FIG. 12, a flow chart is provided that illustrates an example of the processing that is performed in one embodiment of the present invention at the server of FIG. 10 to enable competitive user interaction between one or more users. In FIG. 12, the server receives one or more requests for a competition by one or more users, as represented by block 260. Each user schedules the competition, as represented by block 262. For instance, a user can access one or more web pages hosted by server 216 and/or the communication system to select a private race for selected group of users or a general race that is open for any user. Alternatively, a single user can select to participate in a race against one or more virtual users, whether or not one of such virtual users is a prior stored race of the user scheduling the race.

The server stores the scheduled race, with associated information about each participant and the time when the race is to begin and/or stop. The server identifies, using an internal clock (not shown), when the competition is to begin, as represented by decision block 264. When the competition is to begin, as represented by decision block 264 being in the affirmative, the server verifies that all participants are logged into the server and/or the communication system, as represented by decision block 266. In some situations, the server provides a grace period between the scheduled time for the competition and when the server begins the competition. Consequently, the server can wait for a period of time, allowing late competitors to begin a session on the server or the communication system, as represented by decision block 268 being in the affirmative. Optionally, the server can notify those logged in participants of competitors that are late. Each logged in participant can select to either begin the competition without these late participants or wait for the latecomers. Based upon the selections of the logged in participants, the server can either begin the competition or wait for one or more of the latecomers before beginning the competition.

In another configuration, the server can determine that a minimum number of participants have logged into the server and/or the communication system and automatically begin the competition. The minimum number of participants can be defined by an administrator of the server and/or the communication system, by the participants of the race as each participant schedules the race, by the user or participant that created or scheduled the race, combinations thereof, and the like.

In still another configuration, the server can automatically begin the race at the scheduled time, no matter the number of participants logged into the server and/or communication system (FIG. 1). Alternatively, the server can automatically terminate the race when a minimum number of participants have not logged into the server and/or the communication system.

When the server determines that all or a minimum number of competitors have logged into the server and/or the communication system or that the start time for the race is reached, the race is initiated by, for example, the server sending a command to each of the computer devices and/or exercise devices to begin the race and to begin tracking the user's performance from the relative start time, as represented by block 270.

Throughout the race, the server and/or the communication system receive user performance information from each computer device and/or exercise device, optionally through use of the translator device, as represented by block 272. Throughout the race, data indicative of the relative positions of the participants in the race is sent to all computer devices and/or exercise devices, such as through use of the translator device to convert data deliverable using or in accordance with the computer communication protocol to data deliverable using or in accordance with the exercise communication protocol, as represented by block 274.

As discussed earlier, the server and/or the communication system determine whether or not the race is to end, as represented by decision block 276. In the event that it is determined that the race is not to end, the server and/or communication system in combination with the exercise devices and/or the computer devices continue to receive competitor position data, display the positions of each competitor to each competitor, and communicate new position data to the server and/or communication system.

Once it is determined that the race is ended since each participant in the race has completed the course, a maximum time period associated with the race has expired, or the like, as represented by decision block 276 being in the affirmative, each computer device and/or exercise device delivers final data indicative of the position of the participant using the respective exercise device and/or computer device to the server and/or communication system, as represented by block 278. Upon receiving the results, the server and/or communication system processes the information and determine a winner, as represented by block 280. The server then communicates the official results of the race to each of computer device and/or exercise device across the network and optionally using the translator device to convert the delivered data from a format consistent with being delivered in accordance with or using a computer communication protocol to a format consistent with being delivered in accordance with or using an exercise communication protocol, as represented by block 282.

Thus, in accordance with the systems and methods of the present invention, competitive user interaction on exercise devices is enabled to allow one or more users to experience a competitive environment. A competitive environment is enabled optionally using a translator that provides a communication between a computer device and an exercise device. An application program located at each computer device and/or each exercise device monitors or tracks the user's performance during the race and displays the relative positions of all the users. A server or other computer device receives all user performance information and processes the information in order to determine a winner. Users may participate in the competitive environment regardless of network latency or when individual users participate in the virtual competition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An exercise system configured to enable a user to perform a physical exercise upon an exercise device, the exercise system comprising:
- a translator device disposed between a computer device and an exercise device, said translator device comprising:
    - means for receiving computer data from said computer device, the computer data including control signals configured to change at least one operating parameter of said exercise device, the computer data being transmitted to said means for receiving computer data from said computer device along a wired data connection between said computer device and said means for receiving computer data and using a computer communication protocol;

means for generating exercise data based upon the received computer data and in accordance with an exercise communication protocol; and means for delivering the exercise data to the exercise device through a wired or wireless connection between said means for delivering and the exercise device.

2. An exercise device as recited in claim 1, wherein the means for generating comprises a microcontroller.

3. An exercise device as recited in claim 1, wherein the means for receiving comprises a communication interface.

4. An exercise device as recited in claim 1, wherein the translator device is integrally formed with the exercise device.

5. An exercise device as recited in claim 1, further comprising:

means for sensing exercise data at the exercise device;

means for generating computer data, based upon the exercise data, in accordance with the computer communication protocol; and means for delivering the computer data to the computer device.

6. An exercise device as recited in claim 1, wherein the means for receiving comprises an RS-232 port.

7. An exercise device as recited in claim 1, wherein the computer communication protocol is a RS-232 protocol.

8. An exercise system configured to enable a user to perform a physical exercise, the system comprising:

an exercise device comprising a movable element configured to enable the performance of an exercise by a user, said exercise device receiving data using an exercise communication protocol;

a computer device communicatively coupled to the exercise device, said computer device storing exercise data to be transmitted using a computer communication protocol; and a translator device communicatively disposed between said exercise device and said computer device, said translator device facilitating communication between said exercise device and said computer device by translating data transmitted over a wired connection from said computer device to said translator device using said computer communication protocol into data deliverable to said exercise device over a wired or wireless connection by said exercise communication protocol, and wherein said computer device delivers data including control signals to said translator device, the control signals being configured to change at least one operating parameter of said exercise device.

9. An exercise system as recited in claim 8, wherein the translator device includes a microcontroller that translates the data.

10. An exercise system as recited in claim 8, wherein the translator device is internal to one of the exercise device or the computer device.

11. An exercise system as recited in claim 8, wherein the exercise communication protocol is an $I^2C$ protocol.

12. An exercise system as recited in claim 8, wherein the computer communication protocol is an RS-232 protocol.

13. An exercise system as recited in claim 8, wherein the translator device includes a first interface configured to communicatively couple with the computer device via a first transmission medium and a second interface configured to communicatively couple with the exercise device via a second transmission medium.

14. An exercise system as recited in claim 13, wherein the first transmission medium and the second transmission medium comprise a transmission medium selected from the group consisting of wireless transmission, radio frequency transmission, fiber-optic transmission, and electrical signal transmission.

15. An exercise system as recited in claim 8, wherein the computer device is remote from the exercise device.

16. An exercise system as recited in claim 8, wherein the computer device is communicatively coupled to the translator device through a network.

17. An exercise system as recited in claim 8, wherein the at least one operating parameter of the exercise device controls said movable element.

18. An exercise system as recited in claim 8, wherein the computer device initiates a diagnostic process upon the exercise device.

19. An exercise system as recited in claim 8, wherein the exercise device delivers exercise data indicative of at least one measurable parameter of the exercise device.

20. An exercise system as recited in claim 8, wherein the exercise device delivers exercise data indicative of at least one measurable parameter of a user using the exercise device.

* * * * *

UNITED STATES PATENT AND TRADEMARK OFFICE
CERTIFICATE OF CORRECTION

PATENT NO.         : 7,166,064 B2
APPLICATION NO. : 09/947193
DATED              : January 23, 2007
INVENTOR(S)       : Watterson et al.

It is certified that error appears in the above-identified patent and that said Letters Patent is hereby corrected as shown below:

Column 24
Line 47, change "214a-214n" to --224a-224n--

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,166,064 B2  Page 1 of 2
APPLICATION NO. : 09/947193
DATED : January 23, 2007
INVENTOR(S) : Watterson et al.

It is certified that error appears in the above-identified patent and that said Letters Patent is hereby corrected as shown below:

Title Page
Page 1, Item 56, References Cited, insert category and reference --FOREIGN PATENT DOCUMENTS WO WO98/32496 7/1998--
Page 3, Column 2, after "IEEE Publication, A" change "Teleobotics" to --Telerobotics--

Column 1
Line 58, change "club" to --clubs--

Column 5
Line 7, change "one" to --on--

Column 8
Line 32, remove "it"
Line 38, remove "still"

Column 13
Line 56, change "92" to --97--

Column 14
Line 4, change "FIG. 3" to --FIG. 2--
Line 62, change "FIG. 6" to --FIG. 7--

Column 15
Line 46, change "84" to --104--

Column 16
Line 24, change "152" to --20--
Line 45, change "84" to --104--

This certificate supersedes the Certificate of Correction issued June 16, 2009.

Signed and Sealed this

Twenty-second Day of June, 2010

David J. Kappos
*Director of the United States Patent and Trademark Office*

Column 21
Line 14, change "196" to --176--

Column 24
Line 47, change "214a-214n" to --224a-224n--